United States Patent
Vermaas et al.

(10) Patent No.: US 12,065,639 B2
(45) Date of Patent: Aug. 20, 2024

(54) EXPRESSION OF FUNCTIONAL BACTERIAL TYPE I FATTY ACID SYNTHASE IN PHOTOSYNTHETIC HOSTS

(71) Applicant: Arizona Board of Regents on behalf of Arizona State University, Scottsdale, AZ (US)

(72) Inventors: Willem Vermaas, Tempe, AZ (US); Tyson Burch, Superior, CO (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 294 days.

(21) Appl. No.: 16/716,306

(22) Filed: Dec. 16, 2019

(65) Prior Publication Data

US 2020/0224152 A1  Jul. 16, 2020

Related U.S. Application Data

(60) Provisional application No. 62/780,164, filed on Dec. 14, 2018.

(51) Int. Cl.
  *C12N 1/20* (2006.01)
  *C12R 1/01* (2006.01)

(52) U.S. Cl.
  CPC .............. *C12N 1/20* (2013.01); *C12N 1/205* (2021.05); *C12R 2001/01* (2021.05); *C12Y 203/01085* (2013.01)

(58) Field of Classification Search
  CPC .. C12N 1/20; C12N 1/205; C12R 1/01; C12Y 203/01085
  See application file for complete search history.

(56) References Cited

U.S. PATENT DOCUMENTS

| | | |
|---|---|---|
| 4,683,195 A | 7/1987 | Mullis |
| 8,465,965 B2 | 6/2013 | Mohammed |
| 8,753,840 B2 | 6/2014 | Vermaas |
| 8,962,300 B2 | 2/2015 | Mohammed |
| 9,683,246 B2 | 6/2017 | Mohammed |
| 10,385,304 B2 | 8/2019 | Flory |
| 10,563,162 B2 | 2/2020 | Flory |
| 2011/0014683 A1 | 1/2011 | Vermaas |
| 2020/0354695 A1 | 11/2020 | Vermaas |

FOREIGN PATENT DOCUMENTS

| | | |
|---|---|---|
| WO | 2008051865 A2 | 5/2008 |
| WO | 2008130437 A2 | 10/2008 |
| WO | 2009003178 A2 | 12/2008 |

OTHER PUBLICATIONS

Camsund et al. (Frontiers in Bioengineering and Biotechnology, vol. 2 Article 40, pp. 1-9).*
Cabruja et al. Open Biology vol. 7: 160277, pp. 1-13).*
*Synechocystis* sp. PCC6803 (last modified May 5, 2003).*
Thelwell et al. (PNAS vol. 95 No. 18, pp. 10728-10733).*
Camsund et al. (Journal of Biological Engineering vol. 8 No. 4, pp. 1-23).*
Huang et al. (Journal of Biological Engineering vol. 7 No. 10, pp. 1-11).*
Peca et al. (Acta Biologica Hungarica 58 (Suppl.), pp. 11-22).*
Boehringer, D. et al. "7.5-Å cryo-EM structure of the mycobacterial fatty acid synthase." Journal of molecular biology 425.5 (2013): 841-849.
Bukhari, Hst, et al. "Evolutionary origins of the multienzyme architecture of giant fungal fatty acid synthase." Structure 22.12 (2014): 1775-1785.
Ciccarelli, L., et al. "Structure and conformational variability of the *Mycobacterium* tuberculosis fatty acid synthase multienzyme complex." Structure 21.7 (2013): 1251-1257.
Clerico, E. M., et al. "Specialized techniques for site-directed mutagenesis in cyanobacteria." Methods in molecular biology 362 (2007): 155-171.
Gago, G., et al. "Fatty acid biosynthesis in actinomycetes." FEMS microbiology reviews 35.3 (2011): 475.
Jenke-Kodama, H., et al. "Evolutionary implications of bacterial polyketide synthases." Molecular biology and evolution 22.10 (2005): 2027-2039.
Leonardi, R, et al. "Coenzyme A: back in action." Progress in lipid research 44.2-3 (2005): 125-153.
Liu, X, et al. "Nickel-inducible lysis system in *Synechocystis* sp. PCC 6803." Proceedings of the National Academy of Sciences 106.51 (2009): 21550-21554.
Magnes, C., et al. "LC/MS/MS method for quantitative determination of long-chain fatty acyl-CoAs." Analytical chemistry 77.9 (2005): 2889-2894.
Minkler, P. E., et al. "Novel isolation procedure for short-, medium-, and long-chain acyl-coenzyme A esters from tissue." Analytical biochemistry 376.2 (2008): 275-276.
Rock, C. O., et al. "Pantothenate kinase regulation of the intracellular concentration of coenzyme A." Journal of Biological Chemistry 275.2 (2000): 1377-1383.
Srinivasan, B, et al. "Extracellular 4'-phosphopantetheine is a source for intracellular coenzyme A synthesis." Nature chemical biology 11.10 (2015): 784.
Sumper, M., et al. "Die Synthese verschiedener Carbonsäuren durch den Multienzymkomplex der Fettsäuresynthese aus Hefe und die Erklärung ihrer Bildung." European Journal of Biochemistry 10.2 (1969): 377-387. With English language summary.
Sun, T, et al. "A novel small RNA CoaR regulates coenzyme A biosynthesis and tolerance of *Synechocystis* sp. PCC6803 to 1-butanol possibly via promoter-directed transcriptional silencing." (2017).

(Continued)

*Primary Examiner* — Robert A Zeman
(74) *Attorney, Agent, or Firm* — Quarles & Brady, LLP

(57) ABSTRACT

Provided herein are compositions and methods for expression of functional bacterial type I fatty acid synthase in photosynthetic hosts for production of activated acyl-CoAs and for use in biofuel production.

4 Claims, 19 Drawing Sheets

(56) References Cited

OTHER PUBLICATIONS

Takeshima, Y. et al. "A novel expression vector for the cyanobacterium, Synechococcus PCC 6301." DNA Research 1.4 (1994): 181-189.

* cited by examiner

FIG. 1, CONTINUED
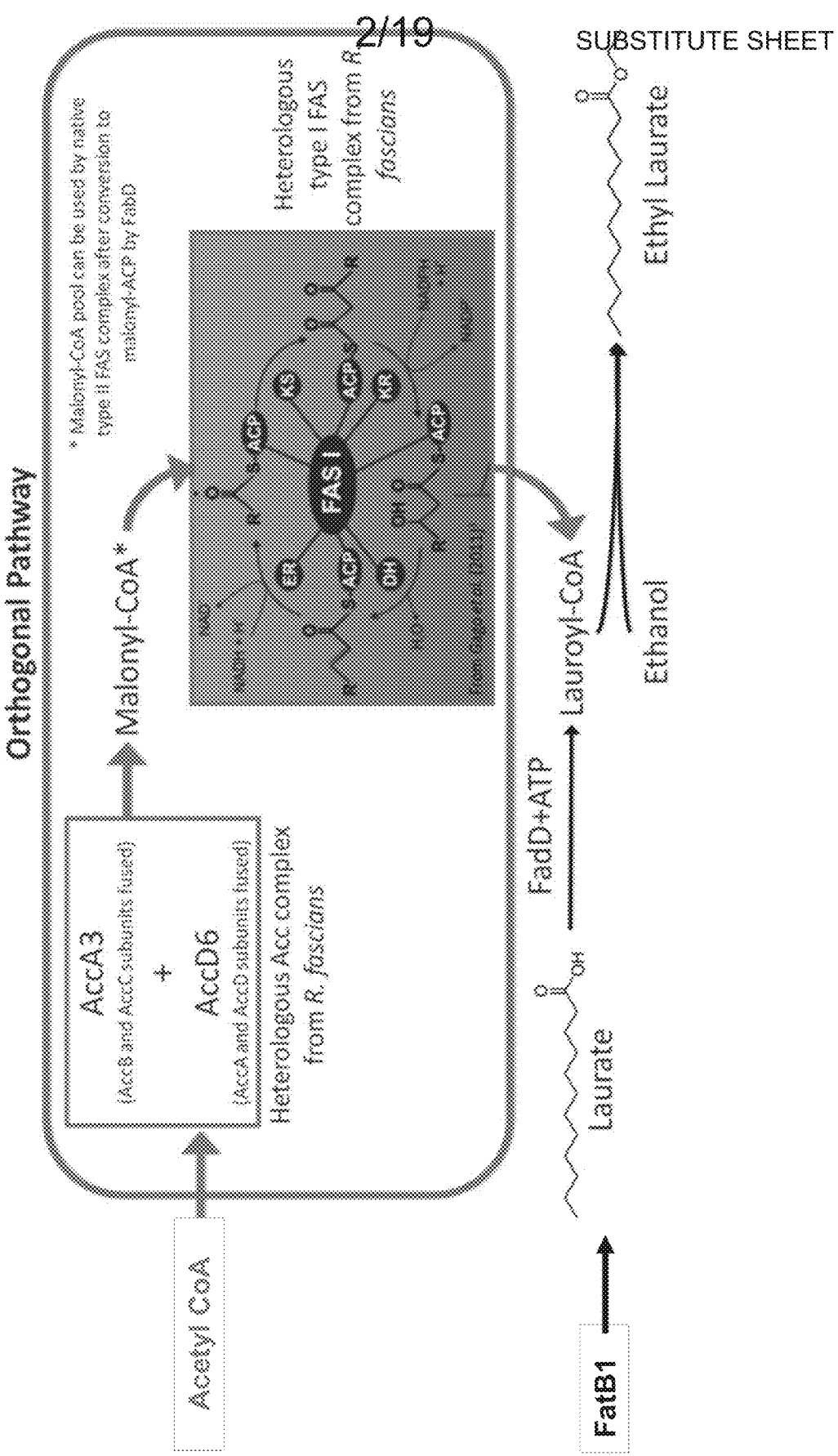

FIGs. 7A-B
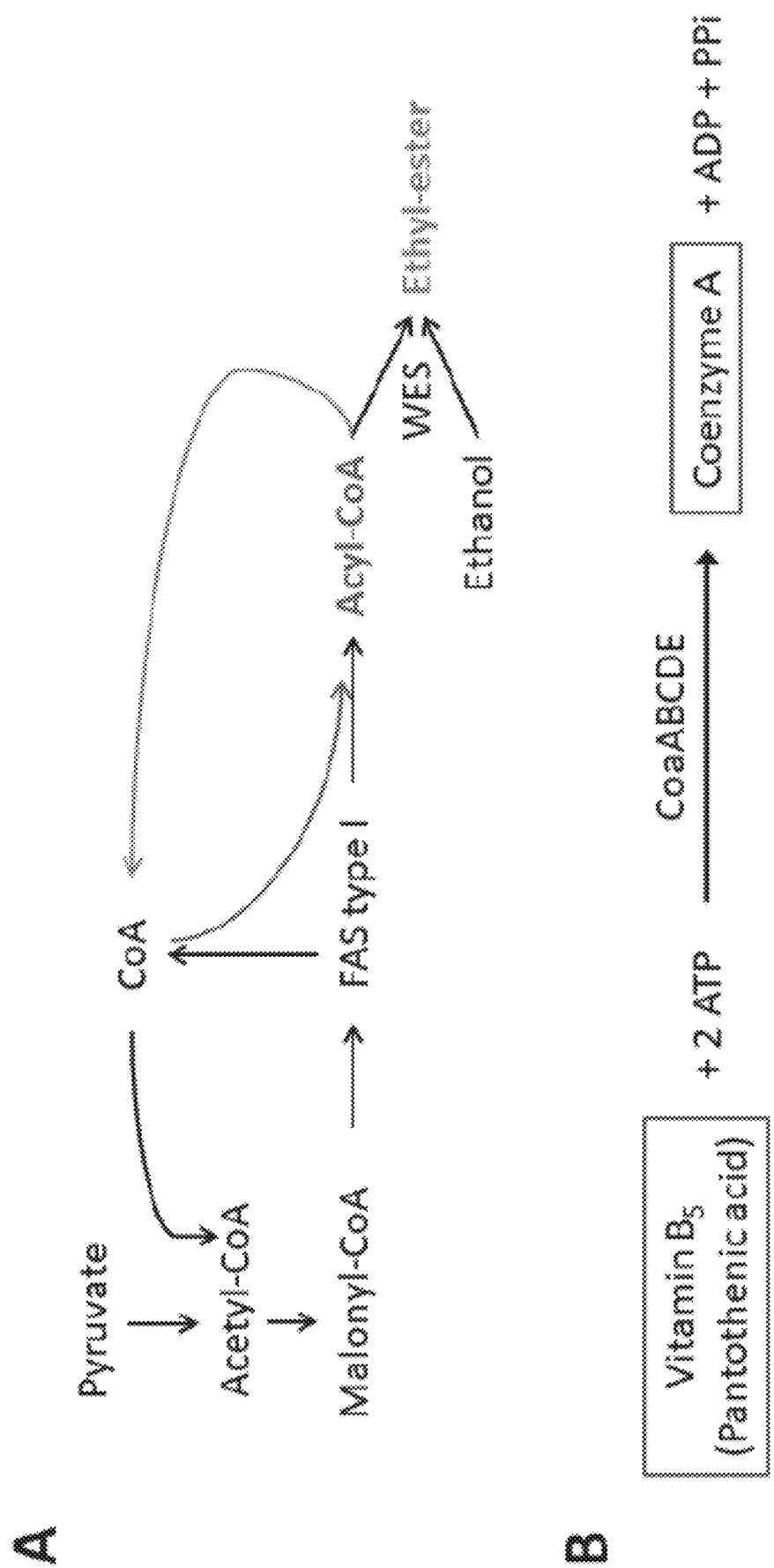

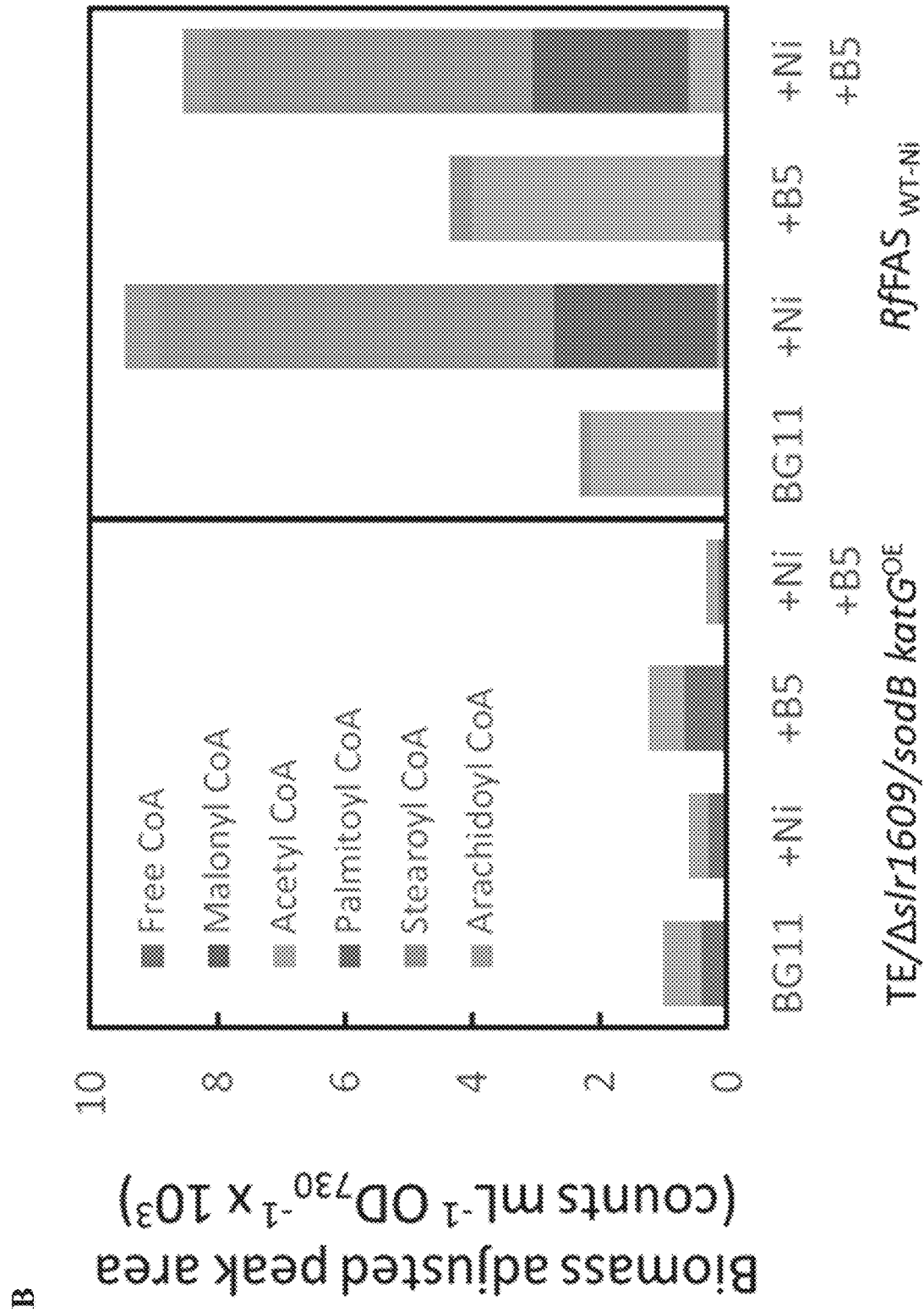
FIGS. 8A-8B, CONTINUED

EXPRESSION OF FUNCTIONAL BACTERIAL TYPE I FATTY ACID SYNTHASE IN PHOTOSYNTHETIC HOSTS

CROSS-REFERENCE TO RELATED APPLICATIONS

This application claims priority to, and the benefit of, U.S. Provisional Patent Application Ser. No. 62/780,164, filed Dec. 14, 2018 which is incorporated herein by reference in its entirety for all purposes.

STATEMENT REGARDING FEDERALLY SPONSORED RESEARCH OR DEVELOPMENT

This invention was made with government support under DE-EE0007561 awarded by the Department of Energy. The government has certain rights in the invention.

BACKGROUND

As petrochemical sources for industrial feedstocks and fuels become scarce, demand for alternative methods of producing biofuel feedstock chemicals will increase. Accordingly, there remains a need in the art for improved methods of producing biofuel feedstock chemicals including precursors for biodiesel production.

BRIEF SUMMARY OF THE DISCLOSURE

In a first aspect, provided herein are genetically engineered photosynthetic cell or organisms that produces activated acyl-CoA. In some cases, the engineered cell or organism is a photosynthetic bacterium genetically modified to comprise one or more transgenes encoding fatty acid synthase type I (FAS I). The photosynthetic bacterium can be *Synechocystis* sp PCC 6803. One or more of the transgenes can be operably linked to an inducible promoter. One or more of the transgenes can be derived from *Rhodococcus fascians* D188 (*R. fascians*). Multiple copies of the one or more transgene gene can be expressed.

In another aspect, provided herein are methods for producing an engineered engineered photosynthetic cell or organism, where the method comprises or consists essentially of introducing into a photosynthetic cell or organism a heterologous gene encoding fatty acid synthase type I (FAS I), wherein the amount of activated acyl-CoA that is produced by the modified photosynthetic cell or organism, is greater than that produced by the unmodified photosynthetic cell or organism. In some cases, the photosynthetic cell or organism is a cyanobacterium such as *Synechocystis* sp PCC 6803. The heterologous gene encoding FAS I can be operably linked to an inducible promoter. The fatty acid synthase type I (FAS I) can be derived from *Rhodococcus fascians* D188. The cyanobacterium can further comprise one or more additional transgenes.

In another aspect, provided herein is a method for producing a acyl-CoA, comprising culturing the modified cyanobacterium produced by the methods of this disclosure. The method can further comprise recovering activated acyl-CoA produced by the modified cyanobacterium.

In another aspect, provided herein is a method for producing activated acyl-CoA, the method comprising the steps of: (a) introducing into a cyanobacterium a heterologous gene encoding fatty acid synthase type I (FAS I), thereby producing a modified cyanobacterium; and (b) culturing the modified cyanobacterium under conditions that promote activated acyl-CoA production by the cyanobacterium. The method can further comprise recovering activated acyl-CoA produced by the cyanobacterium. The cyanobacterium can be *Synechocystis* sp PCC 6803. The fatty acid synthase type I (FAS I) can be derived from *Rhodococcus fascians* D188. The fatty acid synthase type I (FAS I) can be operably linked to an inducible promoter.

In a further aspect, provided herein is a Synechococcus strain being capable of enhanced production of activated acyl-CoA, wherein the strain comprises a heterologous gene encoding fatty acid synthase type I (FAS I). The strain can be *Synechocystis* sp PCC 6803.

BRIEF DESCRIPTION OF THE DRAWINGS

FIGS. 7A-7B provide an illustration of Ethyl-ester (A) and Coenzyme A (B) production pathways. (A) Ethyl-ester production pathway utilizing a FAS type I enzyme, specifically depicting how the CoA pool may be sequestered by acyl-CoA production and recycled by completion of the ethyl-ester production pathway. This recycle mechanism would be expected in any pathway utilizing the acyl-chain and releasing the CoA. Coenzyme A production pathway through conversion of Vitamin $B_5$ (pantothenic acid) by the five CoA synthesis enzymes (CoaABCDE). While the data presented show that the CoA pool and acyl-CoA production are increased by vitamin $B_5$ supplementation, overexpression and/or improvement of the CoA synthesis pathway is another potential method to the same outcome.

Figure 1:
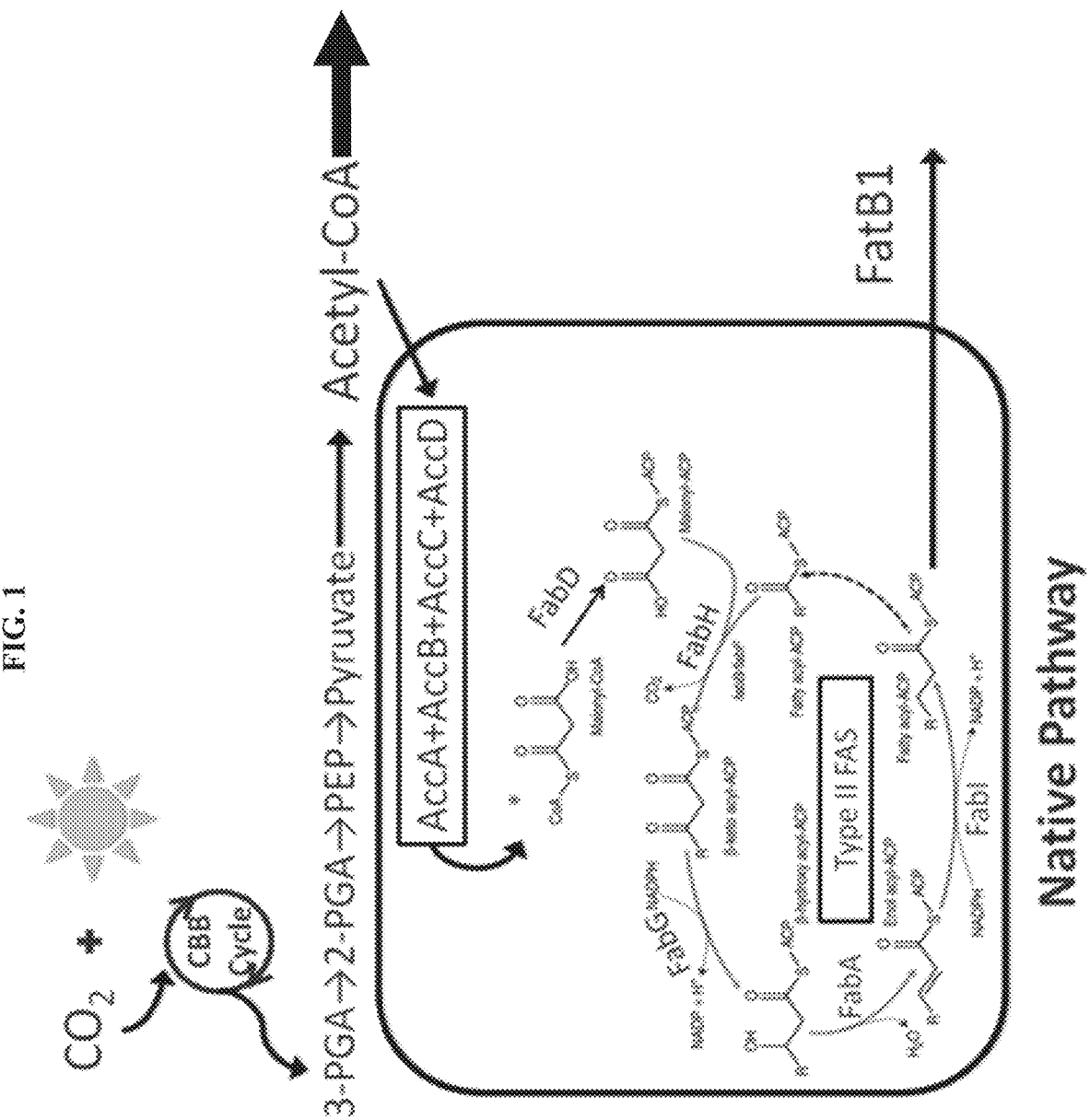
FIG. 1 is a schematic diagram comparing the native fatty acid biosynthesis pathway (left) of *Synechocystis* sp. PCC 6803 with an orthogonal pathway (right) producing acyl-CoAs, where the orthogonal pathway comprises expression of a heterologous FAS I and provides a "one-stop-shop" for photosynthetic biodiesel production. The inset box provides an illustration of a bacterial 1.9 MDa homohexameric FAS type I with its six functional sites (KS, ketoacyl synthase; KR, ketoacyl reductase; DH, dehydratase; ER, enoyl reductase; AT, acetyl transferase; MAT, malonyl-acyl-transferase), and its covalently attached ACP (acyl carrier protein).

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

The compositions and methods provided herein are based at least in part on the inventors' development of genetically modified photosynthetic bacteria that produce acyl-CoAs utilizing a fatty acid synthase type I (FAS I) from *Rhodococcus fascians* D188(*R. fascians*). This is the first known introduction of a functional FAS I in photosynthetic host of any kind. These precursors are useful for production of a variety of chemicals when coupled with additional conversion enzymes. In addition, the precursors themselves are valuable feedstock chemicals. Without being bound to any particular theory or mechanism of action, it is believed that a key advantage of utilizing a bacterial FAS type I pathway in place of the native fatty acid biosynthesis pathway is that the orthogonal FAS type I pathway may be outside the control mechanisms of the cell, improving productivity and eliminating inhibition. The orthogonal FAS pathway is structurally different and produces acyl-CoAs of various chain lengths and for which no FadD is required for conversion of fatty acids to activated acyl-CoAs.

Genetically Engineered Photosynthetic Cell or Organism for Production of Activated Acyl-CoA In one aspect, this disclosure provides genetically engineered photosynthetic cells or organisms comprising an exogenous nucleic acid sequence (e.g., a transgene) encoding one or more key enzymes for synthesizing acyl-CoAs and, more particularly for producing activated acyl-CoAs utilizing an orthogonal FAS type I pathway. As used herein, the term "activated acyl-CoA" refers to any activated fatty acid coupled to Coenzyme A (CoA) and encompasses C:2-CoA through C:22-CoA, particularly Palmitoyl-CoA, Stearoyl-CoA, and Arachidoyl-CoA. Acetyl- and Malonyl-CoA are the precursors for de novo synthesis and elongation and fatty acids by FAS type I.

As used herein, the term "photosynthetic organism" includes an organism, whether single or multi-cellular, capable of carrying out the photosynthetic process of harnessing light energy to induce photochemical oxidation of water molecules to generate electrons. Photosynthetic organisms include, without limitation, plants and microorganisms such as algae, cyanobacteria, and phototropic and chemoautotropic proteobacteria. As used herein, the term "photosynthetic cell" includes a single cell, whether a whole single-cellular organism or a single cell of a multicellular organism (e.g., isolated from such organism), capable of carrying out the photosynthetic process. Thus, in some instances, a photosynthetic cell is also a photosynthetic organism (e.g., a cyanobacterium).

In certain embodiments, the photosynthetic organism is bacterium (e.g., cyanobacterium). In such cases, the genetically modified photosynthetic organism is a photosynthetic bacterium comprising one or more exogenous nucleic acids encoding a FAS Type I gene. As used herein, the term "FAS Type I" means fatty acid synthases of Type I systems, in which a multifunctional enzyme complex comprises discrete functional domains that act as catalytic centers, either on a single polypeptide chain or, in some cases, on two different multifunctional proteins of comparable size. Type I FAS is found in mammals, fungi, and coryneform bacteria, such as members of the genera *Corynebacterium*, *Mycobacterium*, and, as described herein, *Rhodococcus*. In Type I FAS systems, pathway intermediates are covalently bound to the multifunctional enzyme complex, which promotes high efficiency of the pathway. Nucleotide and amino acid sequences for bacterial FAS Type I genes are available at the National Center for Biotechnology Information (found at ncbi.nlm.nih.gov on the World Wide Web). R.f FAS type I: GenBank accession number CP015235 REGION: 3747589..3756888. R.f. acpS: Gen Bank accession number CP015235 REGION: 3756888..3757280.

In certain embodiments, the photosynthetic organism is bacterium (e.g., cyanobacterium). In such cases, the genetically modified photosynthetic organism is a photosynthetic bacterium comprising one or more exogenous nucleic acids encoding a FAS Type I gene. As used herein, the term "FAS Type I" means fatty acid synthases of Type I systems, in which a multifunctional enzyme complex comprises discrete functional domains act as catalytic centers, either on a single polypeptide chain or, in some cases, on two different multifunctional proteins of comparable size. Type I FAS is found in mammals, fungi, and coryneform bacteria, such as members of the genera *Corynebacterium, Mycobacterium*, and, as described herein, *Rhodococcus*. In Type I FAS systems, pathway intermediates are covalently bound to the multifunctional enzyme complex, which promotes high efficiency of the pathway. Nucleotide and amino acid sequences for bacterial FAS Type I genes are available at the National Center for Biotechnology Information R f. FAS type I: GenBank accession number CP015235 REGION: 3747589..3756888. R.f acpS: Gen Bank accession number CP015235 REGION: 3756888..3757280.

It will be understood that various host cells can be genetically modified to produce acyl-CoAs as products or as precursors to products. In some cases, the host cell is a photosynthetic organism such as, for example, a cyanobacterium. Cyanobacteria, also called blue-green algae, belong to a group of prokaryotes performing photosynthesis using their chlorophylls. Exemplary cyanobacteria for genetic modification as described herein include, without limitation, cyanobacteria belonging to *Synechocystis*, Synechococcus, Prochlorococcus, *Acaryochloris, Cyanothece*, and *Anabaena*. In some cases, the cyanobacterium is the unicellular cyanobacterium *Synechocystis* sp PCC 6803, which is a strain of cyanobacteria that was originally isolated from a freshwater lake in 1968 and is available from ATCC as ATCC® 27184™. *Synechocystis* sp PCC 6803 cyanobacteria are highly amenable to genetic modification and demonstrate versatile carbon metabolisms, growing under photoautotrophic, mixotrophic, and heterotrophic conditions. Furthermore, genetic modifications in *Synechocystis* sp PCC 6803 cyanobacteria are quite stable. Because *Synechocystis* PCC6803 lacks certain acyl-CoA breakdown pathways, it may be more preferable to other photosynthetic hosts. It is believed that this disclosure reports the first instance of a bacterial type I FAS being functionally expressed in a photosynthetic host. Other well-suited hosts include Synechococcus sp PCC 7002 and Synechococcus sp. PCC 7942.

In some cases, a transgenic host cell of this disclosure is obtained by introducing into the host cell an orthogonal FAS type I pathway, whereby the transformed host cell produces activated acyl-CoAs utilizing a fatty acid synthase type I (FAS I). In some cases, the orthogonal FAS type I pathway is derived from a species of *Mycobacterium, Corynebacterium*, or *Rhodococcus*. *Rhodococcus* is a genus of aerobic, non-sporulating, non-motile, Gram positive bacteria closely related to *Mycobacterium* and *Corynebacterium*. While the data presented herein demonstrate use of FAS type I from *Rhodococcus fascians* (*R. fascians*) sp. D188, it will be understood by ordinary practitioners in the art that nucleic acid sequence encoding any bacterial FAS type I polypeptide can be used. Many bacterial type I FAS proteins are appropriate for use according to this disclosure. In some cases, bacterial FAS I is selected from one or more of the following species: *Rhodococcus fascians, Cryptococcus neoformans, Ustilago maydis, Corynebacterium glutamicum, C. efficiens, C. ammoniagenes, Gordonia terrae, G. amicalis, Mycobacterium smegmatis, M tuberculosis, M bovis, Nocardia asteroides, N. brasiliensis, Rhodococcus wratislaviensis*, and *R. rhodochrous*. Without being bound by any particular theory or mode of action, it is believed that the native environment of the type I FAS source organism may play a role in the effectiveness of the type I FAS in the transgenic host, depending on the growth environment of the host.

Any vector backbone comprising neutral sites for insertion of one or more nucleic acid sequences of interest can be used for construction of a vector for introduction into a host cell.

Vectors for transformation of microorganisms in accordance with the provided methods can be prepared by known techniques familiar to those skilled in the art. In some cases, the transgene comprises a bacterial FAS Type I gene. In other cases, the transgene further comprises an associated acyl carrier protein (ACP) synthase acpS. In some cases, a nucleic acid as described herein is introduced by physiological transformation and homologous recombination (Cierico et al., *Methods in Mol. Biol.* 362:155-171 (2007)) or by introducing one or more plasmids capable of replicating in cyanobacterial strains of interest (see, for example, Takeshima et al., *DNA Res.* 1:181-189 (1994)). In some cases, transgenes introduced into photosynthetic bacteria may be targeted to plasmid or chromosomal sites.

In some cases, expression of FAS type I is controlled by an operably linked promoter. Various promoters can be operably linked with a nucleic acid comprising the coding region of the gene product of interest in the vectors to drive expression of the gene product of interest in accordance with embodiments herein. As used herein, the term "expression" includes any step involved in the production of a polypeptide including, but not limited to, transcription, post-transcriptional modification, translation, post-translational modification, and secretion. As used herein, the term "operably linked" refers to a linkage in which the expression control sequence is contiguous with the gene of interest to control the gene of interest, as well as expression control sequences that act in trans or at a distance to control the gene of interest. Typically, gene expression is placed under the control of one or more expression control sequences, for example, without limitation, constitutive or inducible promoters, tissue-specific regulatory elements, and enhancers. A gene or coding region is said to be "operably linked to" or "operatively linked to" or "operably associated with" the expression control sequences, meaning that the gene or coding region is controlled or influenced by the expression control sequence. For instance, a promoter is operably linked to a coding sequence if the promoter is capable of affecting the expression of that coding sequence (i.e., the coding sequence is under the transcriptional control of the promoter). Transformation vectors can also contain a second gene that encodes a protein that, e.g., imparts resistance to antibiotic or other selectable marker. Optionally, one or more genes can be followed by a 3' untranslated sequence containing a polyadenylation signal. Expression cassettes encoding the transgenes can be physically linked in the vector or on separate vectors.

A promoter can generally be characterized as either constitutive or inducible. Constitutive promoters are generally active or function to drive expression at all times (or at certain times in the cell life cycle at the same level. Inducible promoters, conversely, are active (or rendered inactive) or are significantly up- or down-regulated only in response to a stimulus. Both types of promoters find application in the methods of this disclosure, but inducible expression may be preferable for the methods of this disclosure because constitutive expression of Type I FAS can lead to Coenzyme A limitation in the transformed host cell. Useful inducible promoters include those that mediate transcription of an operably linked gene in response to a stimulus, such as an exogenously provided element (e.g., $Ni^{2+}$, $Co^{2+}$, $Zn^{2+}$, $Cu^{2+}$), temperature (heat or cold), the presence or absence of a culture condition, etc. As demonstrated in the Examples, a useful inducible promoter for controlled expression of Type I FAS is a nickel-inducible promoter. In some cases, a nickel-inducible promoter and two nickel transport genes derived from *Synechocystis* form a promoter driving the expression of Type I FAS from *Rhodococcus fascians* D188. Accordingly, a transgenic cyanobacterium as described herein can further comprise a nickel (Ni)-regulated promoter (Liu and Curtis, *Proc. Natl. Acad. Sci. USA* 106:21550-21544 (2009)), or other regulated promoter for Ni-induced or otherwise regulated expression of Type I FAS.

Promoters useful herein may come from any source (for example, viral, bacterial, fungal, protist, animal). The promoters contemplated herein can be specific to photosynthetic organisms, non-vascular photosynthetic organisms, and vascular photosynthetic organisms (for example, algae, flowering plants). It will be understood that selection of a particular type of promoter (e.g., inducible, constitutive) may vary depending on the particular application. Preferred promoters activate transcription of an essentially silent gene or upregulate transcription of an operably linked gene that is transcribed at a low level. Exogenous and/or endogenous ("native") promoters that are active in cyanobacteria include, without limitation, psbA2, rbc, cpc (plastocyanin), and trc promoters.

In some embodiments, the promoter is operably linked to a polynucleotide encoding one or more polypeptides of interest. To increase expression from the promoter in vectors in accordance with embodiments herein, the promoter can comprise a transcriptional enhancer.

Genes for transformation into a host cell of interest (e.g., a photosynthetic bacterium) are typically in the form of a DNA or polynucleotide construct comprising the promoter sequences described herein, an operably linked polypeptide encoding sequence described herein, and an operably linked RNA transcriptional terminator sequence. In preparing nucleic acid constructs or an expression cassette for transformation into a photosynthetic bacterium, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g. transitions and transversions may be involved.

In some cases, it nay be useful to synthesize nucleic acids, either completely or in part, by methods known in the art. For example, all or a portion of nucleic acids of this disclosure may be synthesized using codons preferred by a selected host. In some embodiments, at least one of the transgenes can comprise codons preferred for expression in cyanobacteria. Species-preferred codons may be determined, for example, from the codons used most frequently in the proteins expressed in a particular host species. Other modifications of the nucleotide sequences may result in mutants having slightly altered activity.

Once the nucleic acid construct of the present invention has been prepared, it may be incorporated into a host cell. Any appropriate transformation method can be used to introduce a nucleic acid (e.g., a transgene) into a cell (e.g., a photosynthetic microorganism such as a cyanobacterium). Exemplary cell transformation techniques include, without limitation, biolistics, electroporation, use of a laser beam, microinjection, glass bead transformation, and silicon carbide whisker transformation. In some cases, co-transformation is used to introduce two or more distinct vector molecules into a cell simultaneously. As used herein, the terms "Microorganism" and "microbe" refer to microscopic unicellular organisms. As used herein, the term "transgene" refers to a gene that comprises a non-native, recombinant, or modified (e.g., engineered) nucleotide sequence for introduction into a microorganism.

The transgenic photosynthetic microorganisms can be cultured in conventional nutrient media modified as appropriate for activating inducible promoters, selecting transformants, or amplifying the FAR polynucleotide. Culture conditions, such as temperature, pH and the like, will be apparent to those skilled in the art. As noted, many references are available for the culture and production of many cells, including cells of bacterial, plant, animal (especially mammalian) and archebacterial origin.

Methods for Producing Activated Acyl-CoA and Fatty Acids

In another aspect, provided herein are methods for using transgenic photosynthetic microorganisms expressing bacterial Type I FAS described herein for producing activated acyl-CoA and derivatives thereof. In one embodiment, a method of activated acyl-CoA production comprises obtaining a host transgenic photosynthetic microorganism comprising one or more transgenes encoding bacterial Type I FAS, and observing the production of activated acyl-CoAs by the transgenic microorganism.

In some cases, method of activated acyl-CoA production further comprises obtaining a transgenic photosynthetic organism in which genes for competing acyl-CoA breakdown pathways have been inactivated in whole or in part.

The methods provided herein can comprise cultivating activated acyl-CoA-producing transgenic microorganisms under appropriate culture conditions and in an appropriate growth medium. For example, when the transgenic microorganism is a transgenic cyanobacterium, the transgenic cyanobacteria can be grown in enclosed bioreactors containing growth medium. Culture vessels can be equipped for sampling to measure cell density, photosynthesis parameters, and for acyl-CoA measurements by any appropriate technique.

Any appropriate method for observing acyl-CoA production can be used.

In some cases, the methods provided herein can further include capturing acyl-CoA produced by the transgenic microorganisms. Any appropriate method of acyl-CoA extraction can be used. Exemplary methods of capturing acyl-CoA from a cyanobacterial culture include, without limitation, extractive distillation or thermal desorption.

As used herein, the term "biomass" refers to material, such as activated Acyl-CoAs, produced by growth and/or propagation of cells. While biomass may contain cells and/or intracellular contents as well as extracellular material, the term additionally includes, without limitation, compounds produced or secreted by a cell.

Uses for Activated Acy-CoAs In another aspect, provided herein are methods for using activated acyl-CoAs produced according to the methods of this disclosure. Fatty acyl-CoA derivatives produced according to the methods of this disclosure may be used to produce a wide variety of products, including biofuels, free fatty acids, esters, alkylresorcinols and alkylpyrones (phenolic lipids), Omega-3 fatty acids, TAGs, chemical surfactants, polymers, nutritional supplements, pharmaceuticals, food additives, and cosmetics, as well as a variety of chemicals that use activated acyl-CoAs as precursors.

In some cases, provided herein are methods for improved production of biofuels. As used herein, the term "biofuel" refers to any fuel that derives from a biological source. Biofuel refers to one or more hydrocarbons (e.g., 1-nonadecene), one or more alcohols, one or more fatty esters or a mixture thereof. Preferably, liquid hydrocarbons are used. As used herein, the term "hydrocarbon" generally refers to a chemical compound containing carbon (C) and hydrogen (H) (and optionally oxygen (O)). Hydrocarbons may be in gaseous, liquid, or solid form, or any combination of these forms, and may have one or more double or triple bonds between adjacent carbon atoms in the backbone. Accordingly, the term includes linear, branched, cyclic, or partially cyclic alkanes, alkenes (e.g., propene, butene, pentene, hexene, heptene, octene, nonene, decene, undecene, dodecene, tridecene, tetradecene, pentadecene, hexadecene, heptadecene, octadecene, nonadecene, eicosene, uneicosene, doeicosene, and isomers and mixtures thereof), lipids, and paraffin. The term also includes fuels, biofuels, waxes, solvents, and oils.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

In the specification and in the claims, the terms "including" and "comprising" are open-ended terms and should be interpreted to mean "including, but not limited to . . . ." These terms encompass the more restrictive terms "consisting essentially of" and "consisting of"

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (TRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

The inventors introduced an orthogonal heterologous pathway to produce activated acyl-CoAs utilizing a fatty acid synthase type I (FAS I) from *Rhodococcus fascians* D188 (*R. fascians*) (FIG. 1). This is the first known introduction of a functional FAS I in photosynthetic host. While this research was geared toward the production of ethylesters utilizing FAS I to produce precursor acyl-CoAs, those precursors are useful to produce a variety of chemicals when coupled with additional conversion enzymes, and the precursors themselves are a valuable product in today's marketplace.

Methods

Plasmid construction: 1000 base pair homology arms spanning slr1496 to sll1397, a putative transposase site that should be neutral for insertion in *Synechocystis*. Any neutral site should work. Other gene insertion strategies would work.

Figure 2:
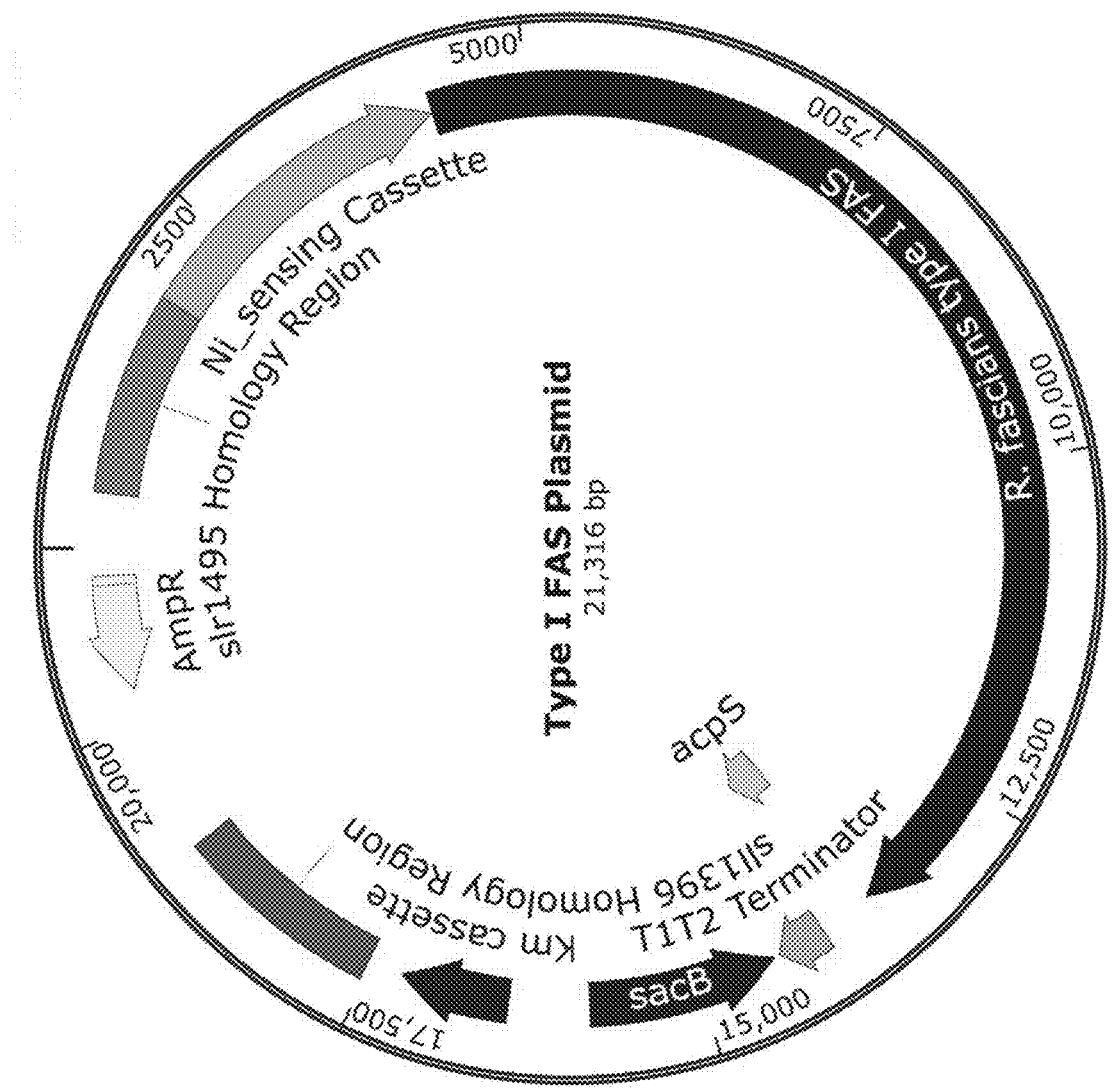
FIG. 2 is a plasmid map of the TyNi vector comprising *R. fascians* type I FAS, after Gibson assembly.

A 21.3 kb plasmid (see FIG. 2) was constructed using nucleic acid sequence encoding *R.fascians* type I FAS plus nucleic acid sequence encoding *R.fascians* Acyl Carrier Protein Synthase (acpS) (9.7 kb). The plasmid comprises high G-C content, approx. 67% GC. A 4-part Gibson assembly was used for construction of the base plasmid. A 3-part Gibson assembly was used for insertion of type I FAS. The plasmid comprises large homology regions for integration into a transposase site, plus a Nickel (Ni)-inducible promoter for controlled expression of *R.fascians* type I FAS. The type I FAS is a very large gene leading to a very large plasmid. Use of NEB 10-3 electrocompetent *E. coli* cells made it possible to produce the very large construct. Other assembly strategies and *E. coli* backgrounds could be used to prepare the construct.

In this example, a kanamycin resistance gene was used as a marker gene; other markers could be used as well as marker-less transformation techniques.

The plasmid was transformed into cyanobacteria using the following *Synechocystis* transformation protocol. Other transformation techniques could potentially work.

Cyanobacterial Transformation
1) Start a fresh culture in BG-11+glucose.
2) Measure $OD_{730}$ after 2-3 days of growth.
3) Spin down cells in sterile 50 mL tube in table-top centrifuge at room temperature.
4) Re-suspend cells in original growth medium (kept sterile) to $OD_{730}$=2.5. (EXAMPLE: Total volume of cells in tube×OD at 730 nm=Total volume of cells plus medium to give $OD_{730}$ of 2.5)
5) Place 0.4 mL of resuspended cells in sterile glass culture tubes.
6) Add 2-8 μL DNA to each tube and shake. Leave one tube as a control (no DNA added).
7) Place the tube rack in the growth chamber at 30° C. for 6 hours. Shake at 3 hours.
8) Plate 200 μL on a sterile filter (Whatman Nuclepore Track-Etch Membrane #111107, 47 mm diameter; 0.4 μM pore size) that has been placed on a BG-11+G plate. Spread cells around.
9) Grow for 24 hours and then transfer the filters to appropriate medium (usually plates containing antibiotics, or plates without glucose).

Figure 11:
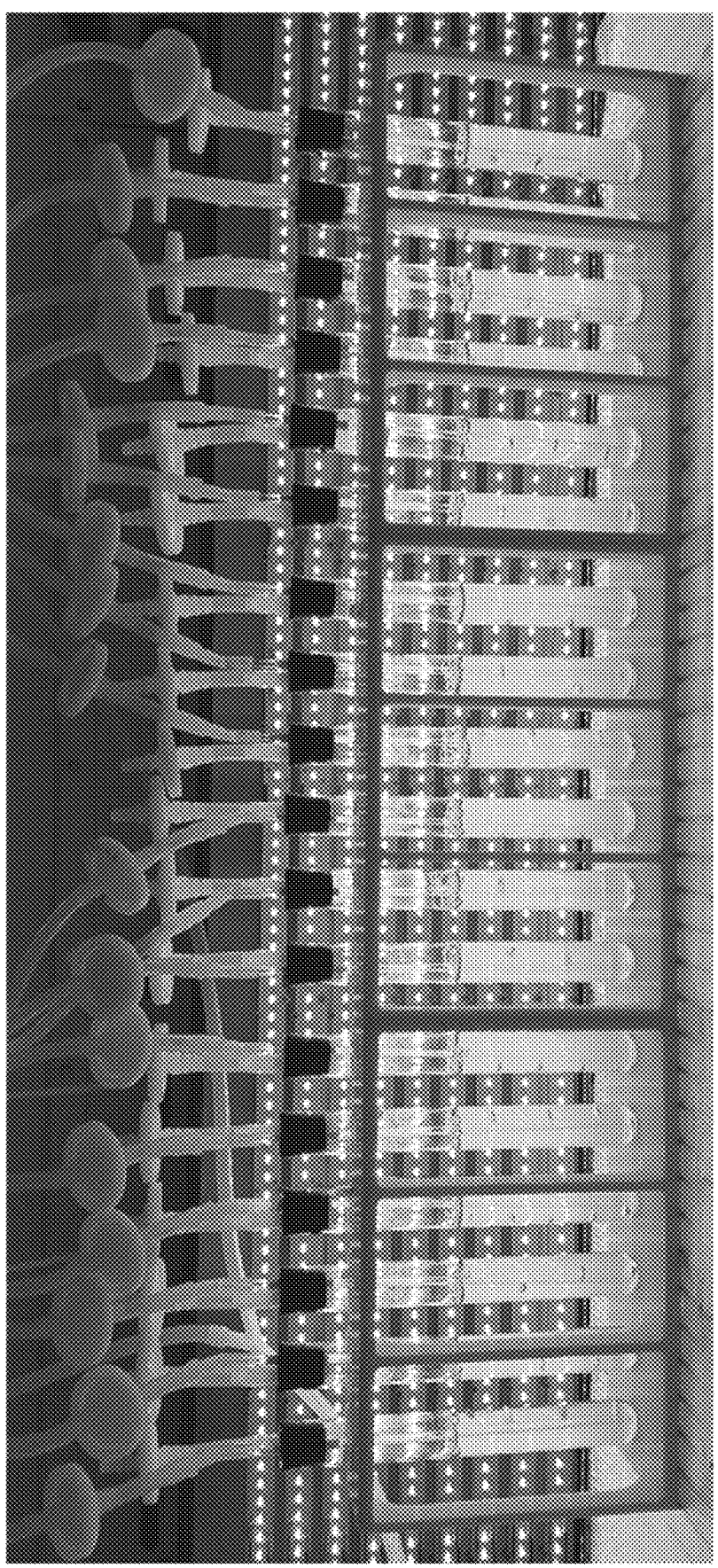
FIG. 11 illustrates an exemplary experimental setup and culture conditions in Tyson Tubes.

After transformation, segregation of the insert was achieved by consecutive re-plating on higher antibiotic concentration plates. Transformed cyanobacteria were cultured using an experimental set-up as shown in FIG. 11.

CoA pool analysis: CoAs were extracted and purified using a neutral pH SPE column protocol developed by Minkler et al. (2008) *Anal. Biochem.* 376:275-276. An exemplary extraction protocol is set forth below. Samples were analyzed by positive ESI LC-MS/MS based on Magnes et al. (2005) *Anal. Chem.* 77:2889-2894.

Extraction Protocol

The literature provides a variety of methods for extracting and preparing short-chain acyl-CoA species or long-chain acyl-CoA species, but relatively few that appear to effectively analyze all acyl-CoA species at once. The extraction protocol described herein is based on a method for extracting short and long-chain acyl-CoA species by using neutral pH elution from a custom-designed Solid Phase Extraction (SPE) column (see Minkler et al. 2008). Cell pellets were processed as follows for extraction and sample preparation for LC/MS.

As quickly as possible, samples were removed from the growth apparatus, 25 mL of the culture, harvest the cells onto a filter (Whatman Nylon Membrane 0.8 μm 47 mm, 7408-004) by means of an aspirator. Quickly immerse the filter (cells down) into a pre-cooled dish that came straight out of the −80° C. freezer and that contains 2 ml-80° C. methanol. Then store the dish in at −80° C. Scrape the cells into a microcentrifuge tube, with the methanol. Quickly centrifuge at 4° C. and remove the supernatant.

1. Add 1.5 mL cold acetonitrile/isopropanol (3+1, v+v) and an appropriate internal standard (a medium-chain acyl-CoA not expected in our samples) to quantify any losses to the extraction procedure.
2. Bead-beat to lyse cells.
3. Add 0.5 mL cold 0.1 M $KH_2PO_4$ pH 6.7 and bead-beat again.
4. Centrifuge and extract portion of the supernatant.
5. Acidify the extracted supernatant by adding glacial acetic acid.
6. Condition SPE column with 1 mL acetonitrile/isopropanol/water/acetic acid (9+3+4+4, v+v+v+v).

7. Add supernatant and flow-through.
8. Rinse with 1 mL acetonitrile/isopropanol/water/acetic acid (9+3+4+4, v+v+v+v).
9. Elute acyl-CoA esters with 2 mL methanol 250 mM ammonium acetate (4+1, v+v) pH 7.
10. Dilute with water, set pH to 3.5-5, and add internal standard for LC-MS/MS analysis.

HPLC Separation

The methods for HPLC separation of acyl-CoAs are varied throughout the literature. Magnes et al. (2005) describe a procedure that uses a Zorbax Extend column that the inventors used for separation, so experiments were performed using the solvent system described in this paper for acyl-CoA separations.

MS/MS Analysis

Figure 3:
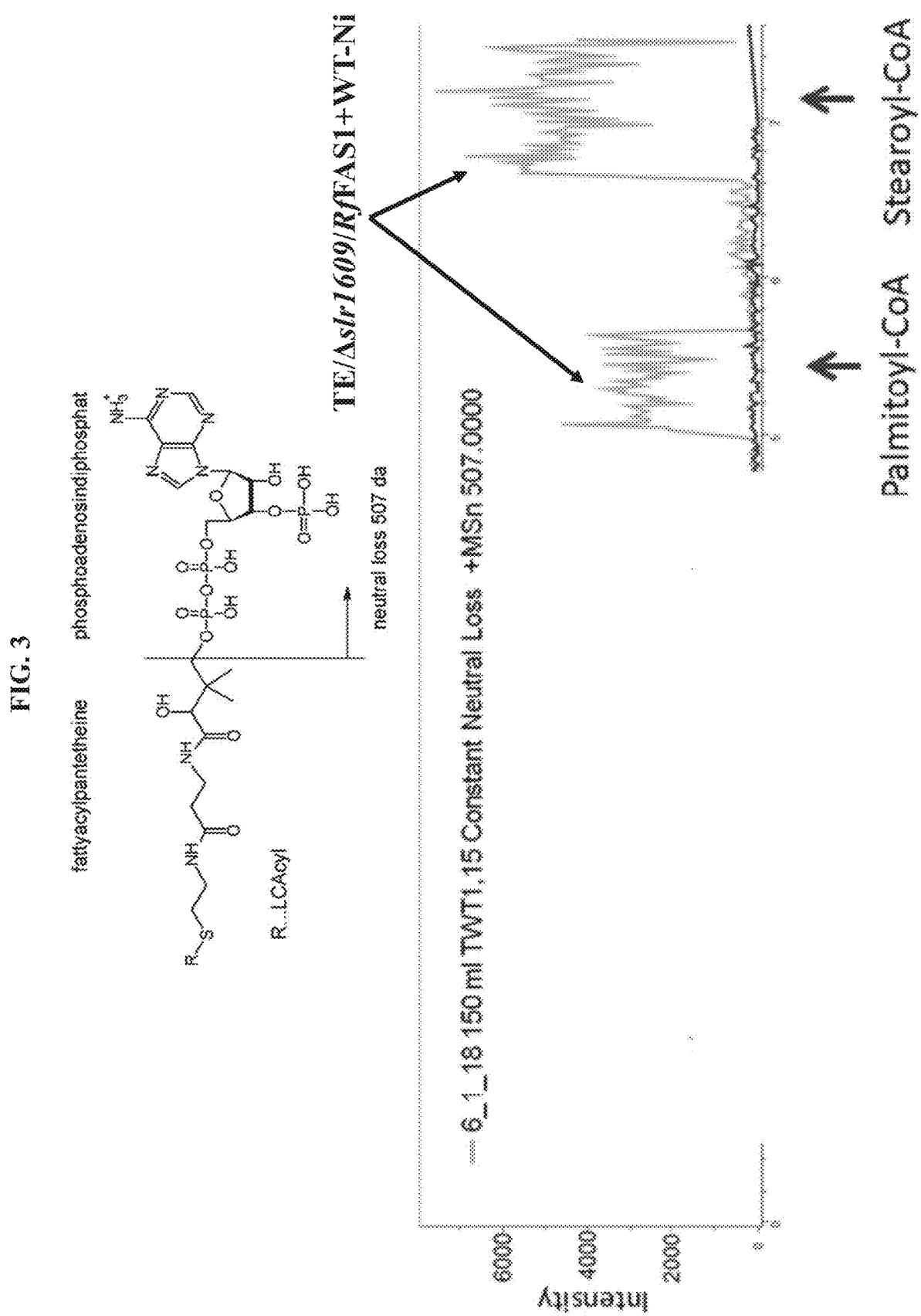
FIG. 3 presents (top) neutral mass loss all CoA species exhibit under positive ESI mode MS/MS and (bottom) traces of detected neutral losses of 507 Da during direct infusion MS-MS over a range of target parent ion masses for acyl-CoAs extracted from the FAS I strain, TE/Δslr1609/Rf-FAS1+WT-Ni. The strain was grown in a 150 mL flat-sided bottle bubbled with 0.3% $CO_2$ and illuminated with 150 μmol photons m−2s-lby by cool white fluorescent bulbs. Palmitoyl- and Stearoyl-CoA peaks are indicated under the X-axis.

Neutral loss traces were generated by the system to identify neutral losses of 507 Da (see FIG. 3) over time. Acyl-CoA peaks and elution times were cross validated through the use of neutral-loss scans and pure standards of various acyl-CoAs.

Results

Figure 4A:
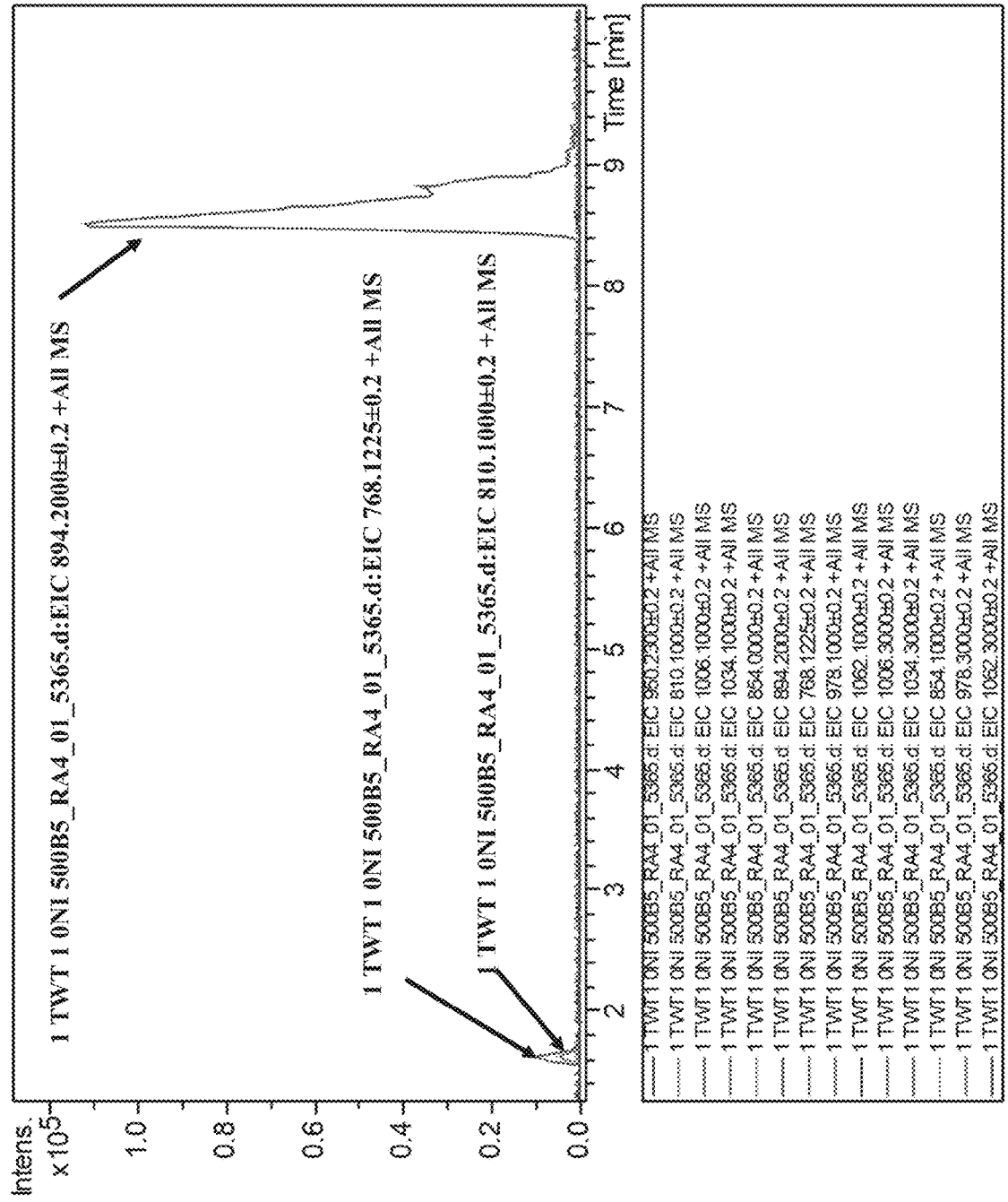
FIGS. 4A-4B present chromatogram traces of parent ion masses in (A) the FAS type I-bearing strain TWT1 with vitamin B5 supplementation but without nickel induction of expression of the type I FAS, exhibiting peaks for free-CoA, acetyl-CoA, and the internal standard, and (B) the type I FAS-bearing TWT1 strain with both vitamin B5 supplementation and nickel induction of the type I FAS, exhibiting peaks for the internal standard, Palmitoyl-CoA, Stearoyl-CoA, and Arachidoyl-CoA.
Figure 4B:
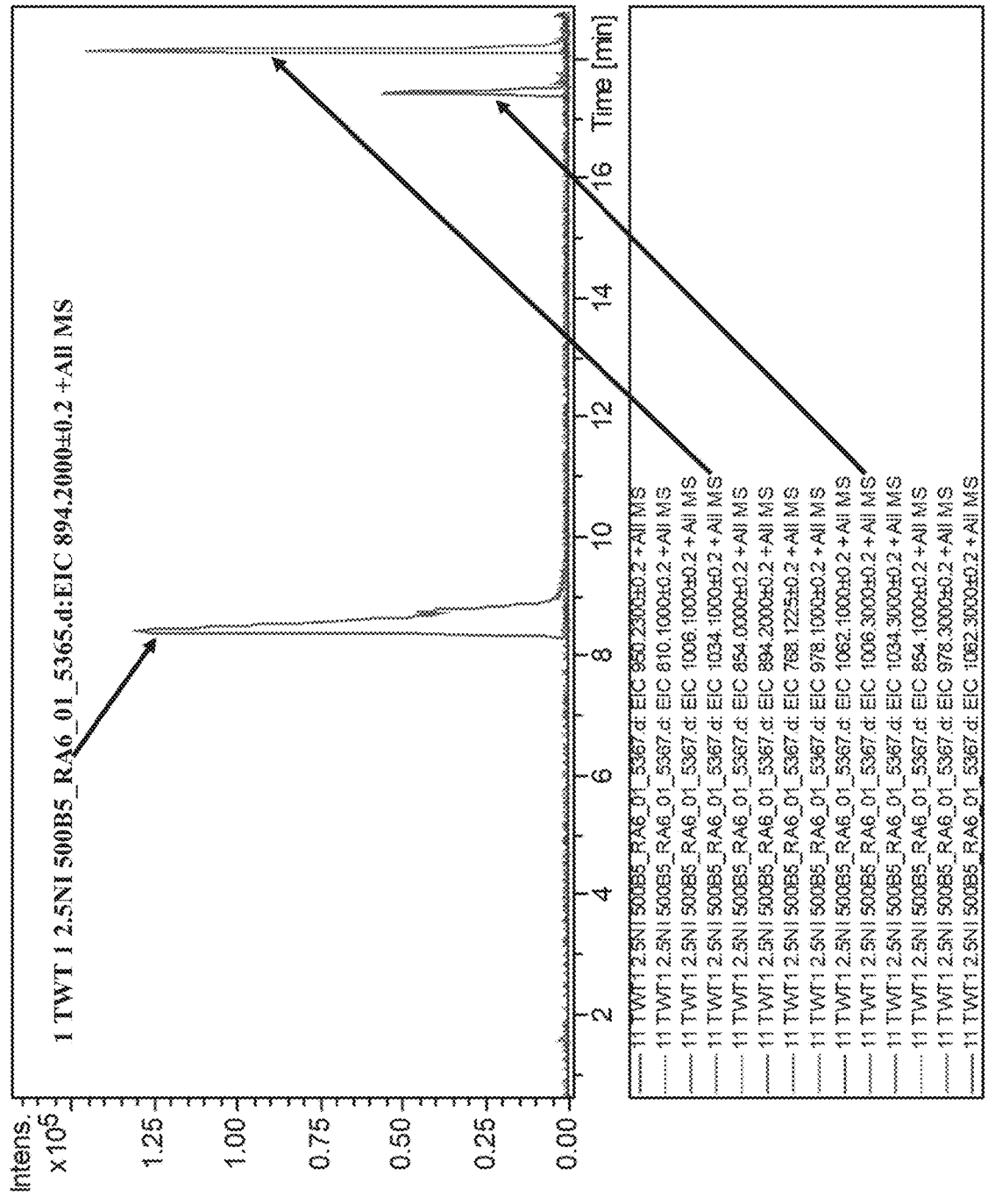
Figure 5A:
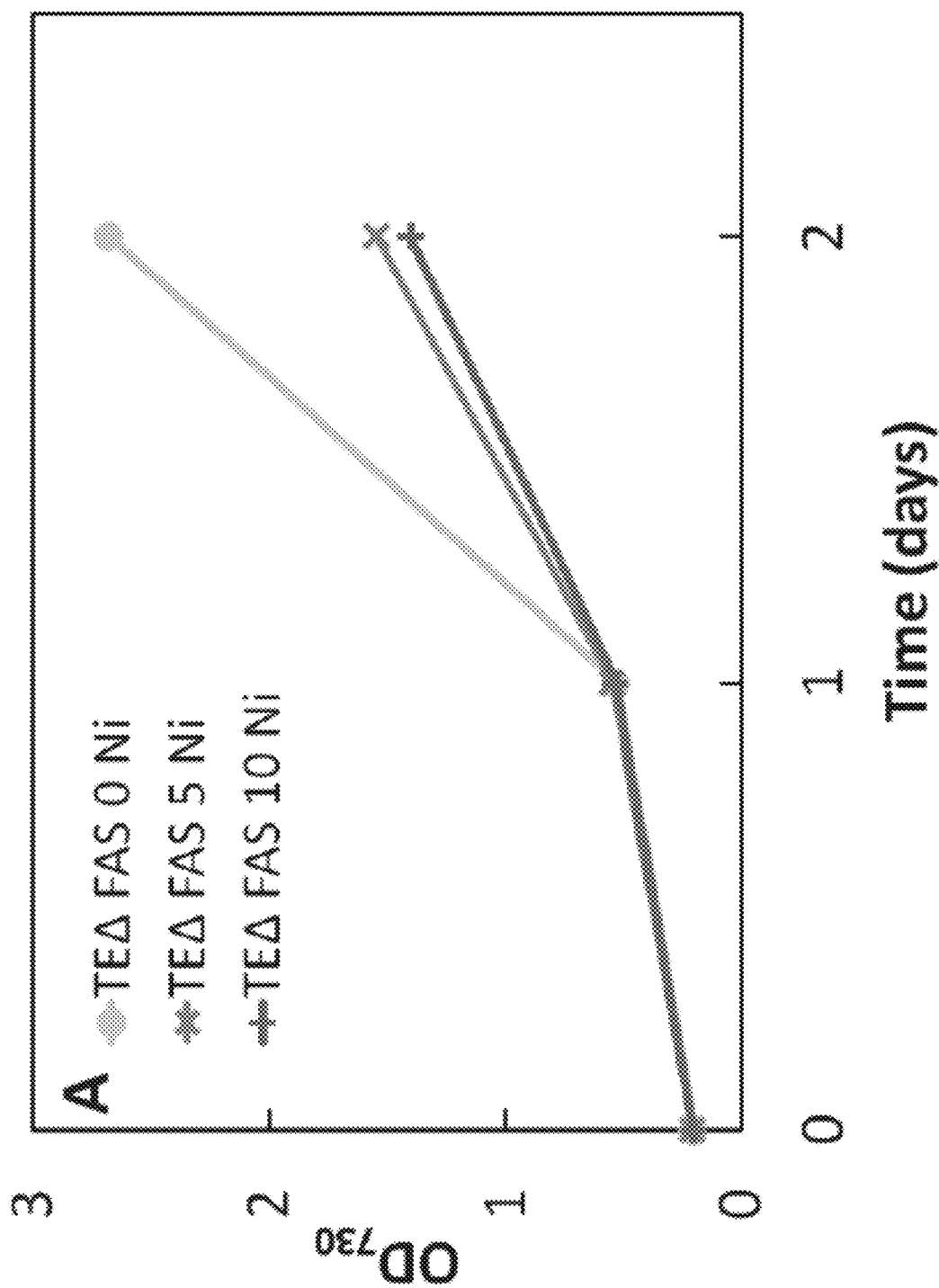
FIGS. 5A-5B show growth rates as measured by Optical Density at 730 nm ($OD_{730}$) over time as a proxy (A) and MS/MS acyl-CoA signal intensity during direct infusion for selected acyl-CoAs (B) in the TE/Δslr1609/RfFAS1+WT-Ni strain. Nickel sulfate (Ni) concentrations used to induce expression of the type I FAS are indicated below the X axis (B). Cultures were grown in 50 mL tubes bubbled with 0.5% $CO_2$ at a light intensity of 150 μmol photons $m^{-2}s^{-1}$ from an LED light source.
Figure 5B:
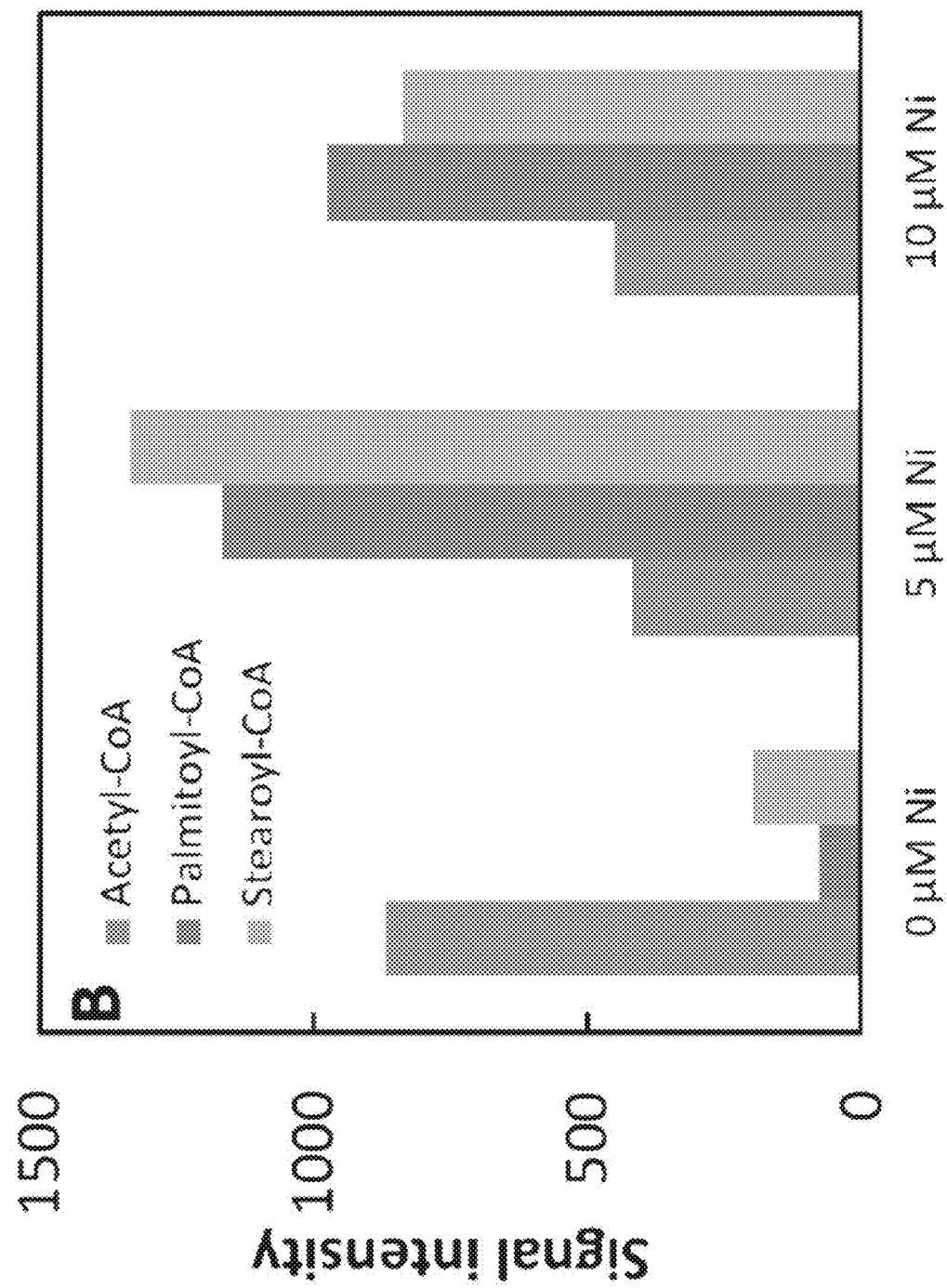

FIGS. 4A-4B show representative results from the LC-MS runs. FIG. 4A shows chromatogram traces of parent ion masses in the FAS type I-bearing strain TWT1 with vitamin $B_5$ supplementation but without nickel induction of expression of the type I FAS, exhibiting peaks for Free-CoA, Acetyl-CoA, and the internal standard. FIG. 4B shows the type I FAS-bearing TWT1 strain with both vitamin B5 supplementation and nickel induction of the type I FAS, exhibiting peaks for the internal standard, Palmitoyl-CoA, Stearoyl-CoA, and Arachidoyl-CoA.

Figure 6:
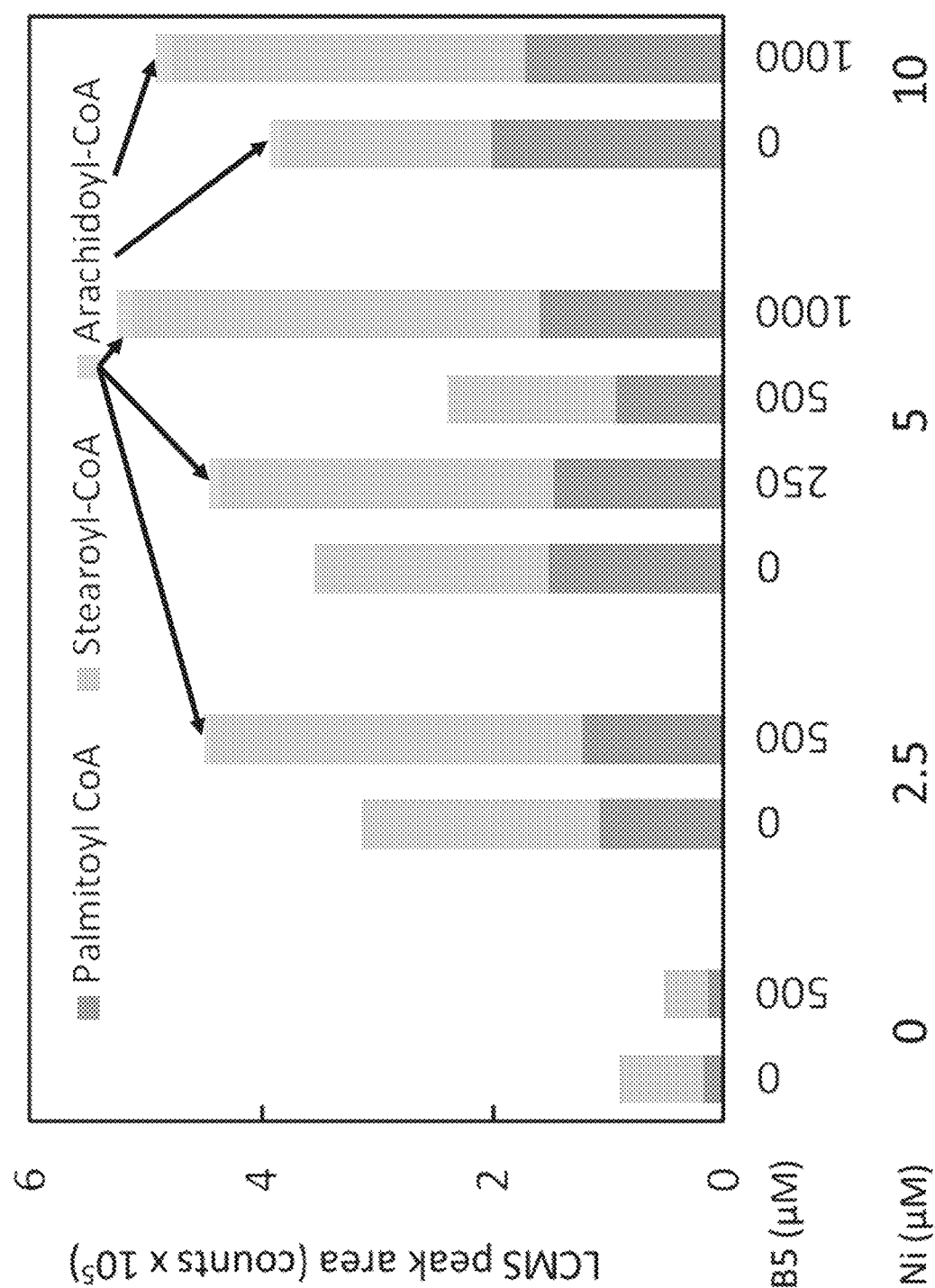
FIG. 6 is a graph demonstrating increased production of Palmitoyl-CoA, Stearoyl-CoA, and Arachidoyl-CoA in the presence of Vitamin B5 and Nickel (Ni) in a dose-dependent manner. The nickel-inducible FAS type I strain TWT1 was grown in 50 mL Tyson Tubes bubbled with 0.5% $CO_2$ at a light intensity of 150 μmol photons $m^{-2}s^{-1}$ from an LED light source for one day with the indicated concentrations of Vitamin $B_5$ (B5) added at time 0, then nickel sulfate (Ni) was/was not added to the cultures at the concentrations indicated, the cultures were grown for one more day, then samples were removed for CoA analysis.
Figures 8A, 8B:
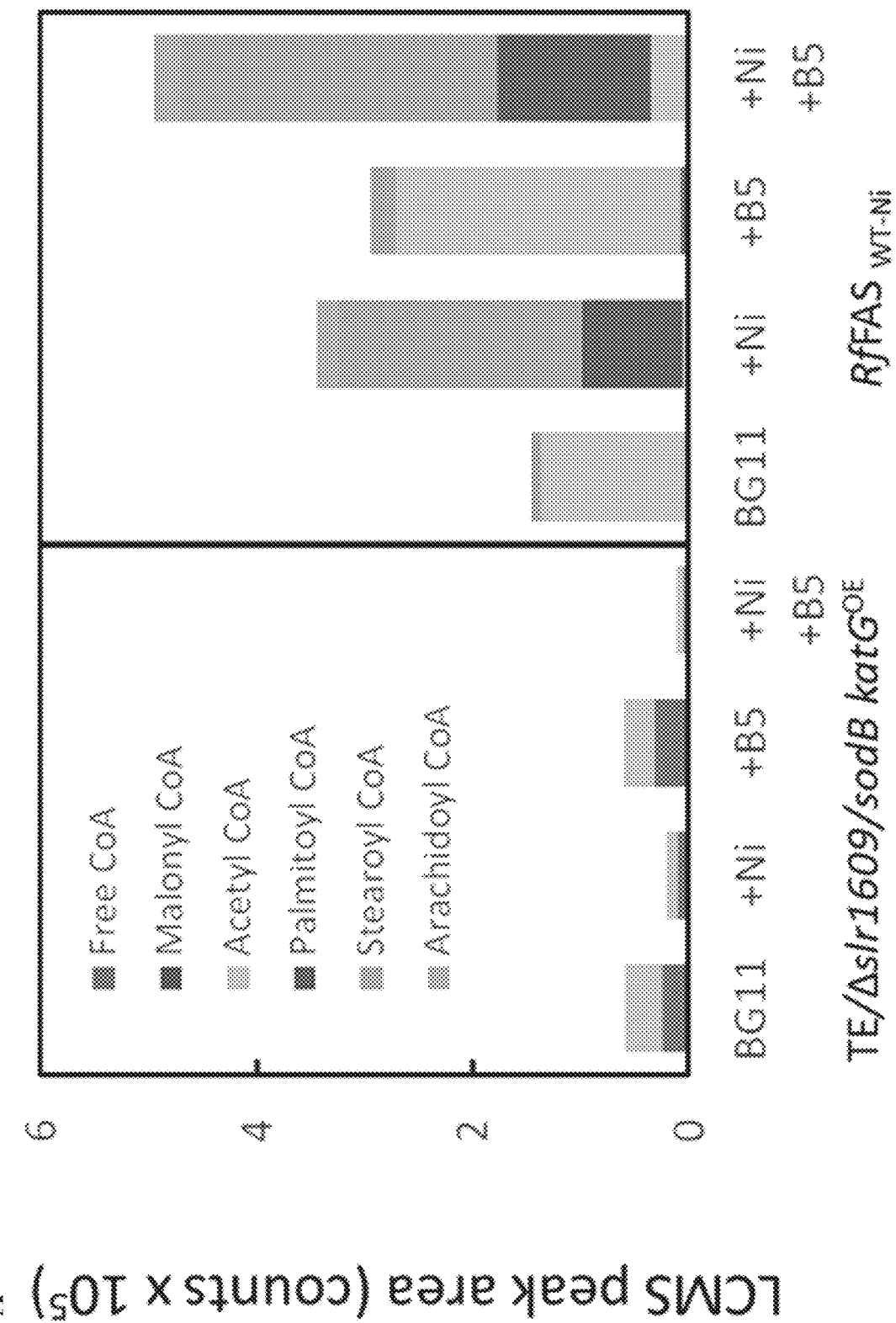
FIGS. 8A-8B presents relative amounts of free and attached CoAs (A) and biomass adjusted amounts of free and attached CoAs (B), for the TE/Δslr1609/sodB+katGOE and RfFAS+WT-Ni (TWT1) strains ±10 μM $NiSO_4$ and ±100 μM Vitamin $B_5$. Cultures were grown under standard conditions in Tyson Tubes (50 mL cultures, 150 μmol photons $m^{-2}$ $s^{-1}$ provided by LED panels, 30° C., 0.5% $CO_2$ at 30 mL $min^{-1}$ gas flow rate per tube). Vitamin $B_5$ was added at time 0, and $NiSO_4$ was added after 24 hours when cultures had an $OD_{730}$ of around 1.
Figure 9:
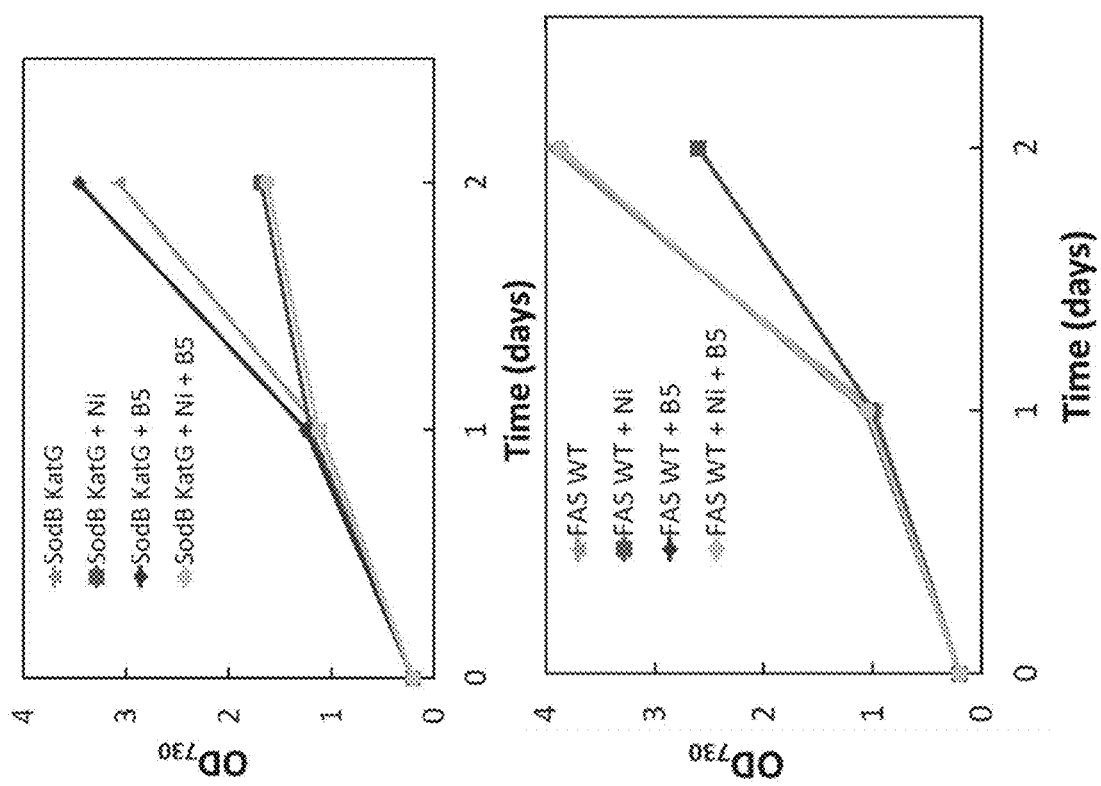
FIG. 9 presents growth rates using $OD_{730}$ over time as a proxy for a laurate producing strain SodB KatG vs the nickel-inducible FAS type I strain TWT1±100 μM Vitamin $B_5$ added at time 0 and +10 μM $NiSO_4$ added at time 1. Cultures were grown under standard conditions in Tyson Tubes (50 mL cultures, 150 μmol photons $m^{-2}$ $s^{-1}$ provided by LED panels, 30° C., 0.5% $CO_2$ at 30 mL $min^{-1}$ gas flow rate per tube).
Figure 10:
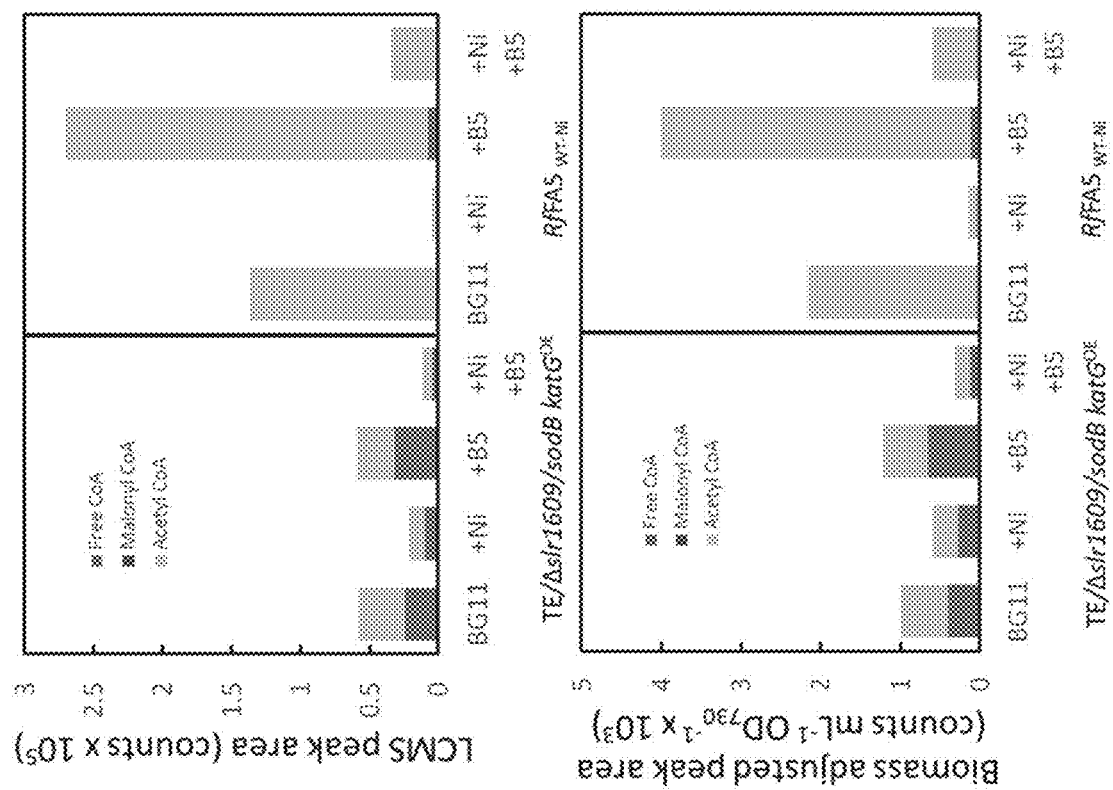
FIG. 10 presents relative and biomass adjusted amounts of free, Malonyl-, and Acetyl-CoA for the TE/Δslr1609/sodB+katGOE and RfFAS+WT-Ni (TWT1) strains ±10 μM $NiSO_4$ and ±100 μM Vitamin $B_5$. Cultures were grown under standard conditions in Tyson Tubes (50 mL cultures, 150 μmol photons $m^{-2}s^{-1}$ provided by LED panels, 30° C., 0.5% $CO_2$ at 30 mL $min^{-1}$ gas flow rate per tube).

Without a pathway to recycle the attached Coenzyme A, FAS I function may deplete the CoA pool (FIGS. 7A, 8, and 10). Adding vitamin B5 (pantothenic acid) to the culture medium appeared to increase the CoA pool in the FAS I wild-type background strain, RfFAS+WT-Ni, but not the laurate-producing strain, TE/Δslr1609/sodB+katG$^{OE}$ (FIGS. 8 and 10). Vitamin $B_5$ appeared to eliminate the growth inhibition caused by nickel induction of FAS I (FIG. 9). Total acyl-CoAs in the culture appeared to be increased by addition of vitamin $B_5$ during nickel induction of FAS I (FIGS. 6 and 8).

As shown in FIG. 9, Ni decreased growth rate in all cultures in the absence of Vitamin $B_5$. Vitamin $B_5$ recovered growth in Ni induced FAS type I cultures, but did recover growth in SodB KatG plus Ni. The inventors concluded that vitamin $B_5$ does not reduce sensitivity to Ni. As shown in FIG. 8B, the addition of Vitamin $B_5$ increased overall acyl-CoA production in the culture, but not on a "per biomass" basis. Instead, Vitamin $B_5$ apparently increased the pool of available CoAs. Acyl-CoA production may still be limited by CoA availability.

As shown in FIG. 10, the addition of Vitamin $B_5$ increased acetyl-CoA in the WT FAS strain but not in sodB katG. No malonyl-CoA was detected in any cultures (though it is detectable). The sodB katG strain may have lower CoA levels in general.

Figures 12A, 12B:
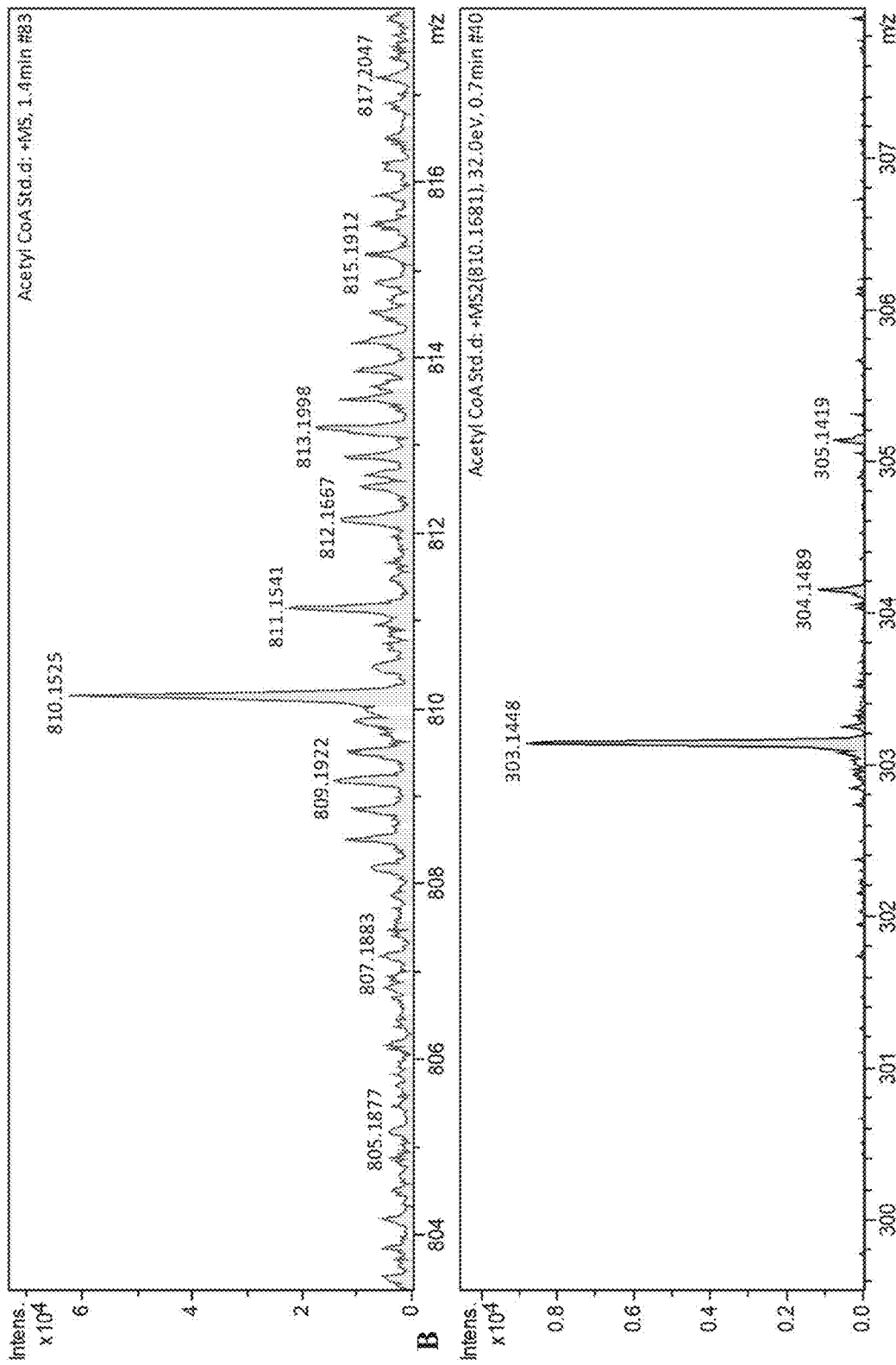
FIGS. 12A-12B demonstrate (A) MS parent ion peak (810 Da) for a 20 μM Acetyl-CoA standard put through the entire extraction and purification process; and (B) MS/MS peak for Acetyl-CoA (303 Da) obtained through collision of the parent ion of 810 Da after a neutral loss of 507 Da.
Figure 13:
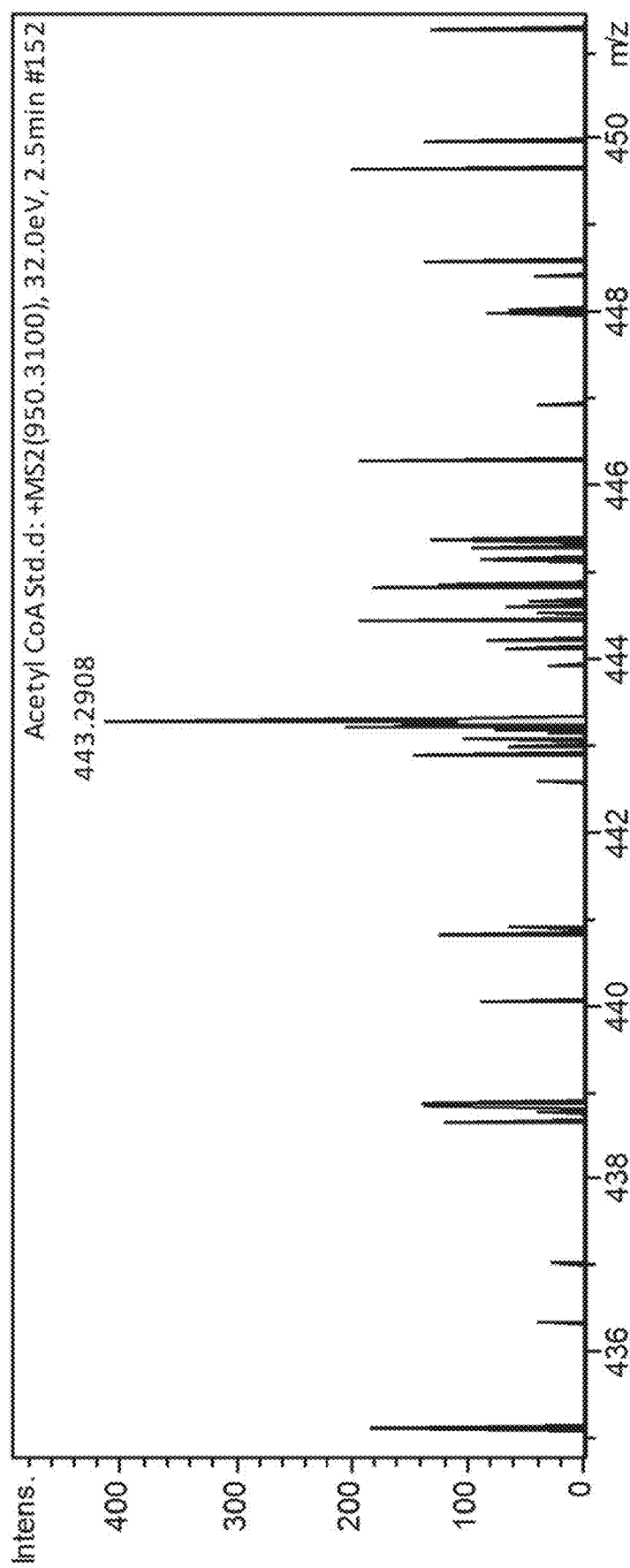
FIG. 13 demonstrates MS-MS peak for Lauroyl-CoA (443 Da) obtained through collision of the parent ion mass of 950 Da after a neutral loss of 507 Da, indicating a possible Lauroyl-CoA impurity in the Acetyl-CoA standard.

Acetyl-CoA Standard. To identify Acetyl-CoA, the parent ion mass in positive ESI mode is 810 Da. Relying on the parent ion peak in normal MS mode alone is unreliable because of the likely presence of confounding salt adducts (resulting from other chemicals because the samples have not been purified through LC; instead they are direct infusions). By adding MS/MS results, it was possible to verify that a parent ion is indeed the CoA species by detecting a neutral loss of 507 Da. For example, the MS/MS peak for Acetyl-CoA should be 303 Da. FIGS. 12A-12B demonstrate detection of 20 μM standards of Acetyl-CoA through the extraction and purification process. Interestingly, it appears Acetyl-CoA may have a slight Lauroyl-CoA impurity as indicated by the MS/MS results in FIG. 13.

Figures 14A, 14B:
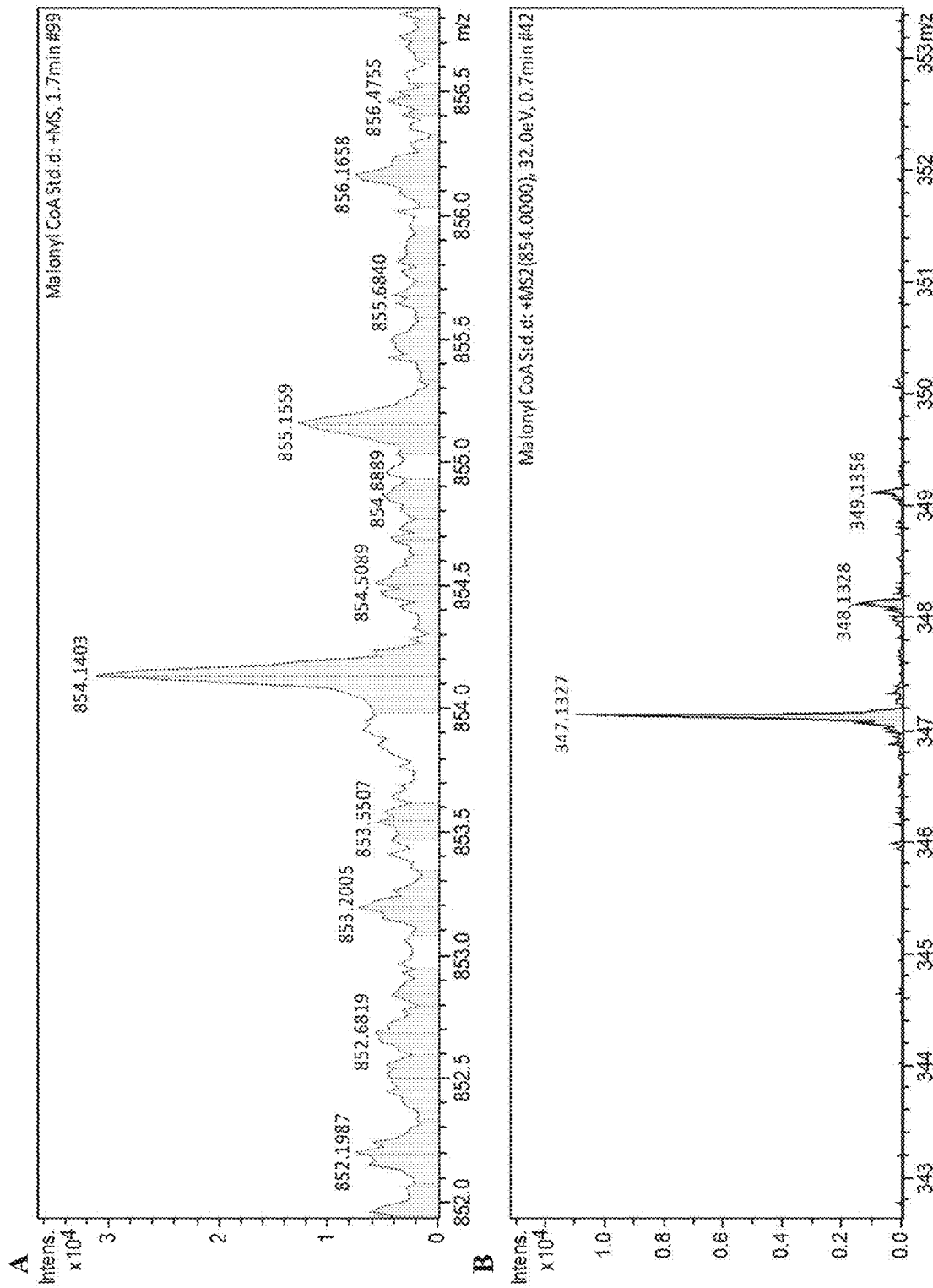
FIGS. 14A-14B demonstrate (A) MS parent ion peak (854 Da) for a 20 μM Malonyl-CoA standard put through the entire extraction and purification process; and (B) MS/MS peak for Malonyl-CoA (347 Da) obtained through collision of the parent ion of 854 Da after a neutral loss of 507 Da.

Malonyl-CoA Standard. FIGS. 14A-14B show the results for a 20 μM standard subjected to an extraction and purification process in both MS (FIG. 15A) and MS/MS (FIG. 15B) mode. The parent ion of Malonyl-CoA is 854 and the MS-MS peak is thus 347 after a neutral loss of 507 Da. These results indicate that Malonyl-CoA is easily detected by the described extraction and quantification methods.

Figures 15A, 15B:
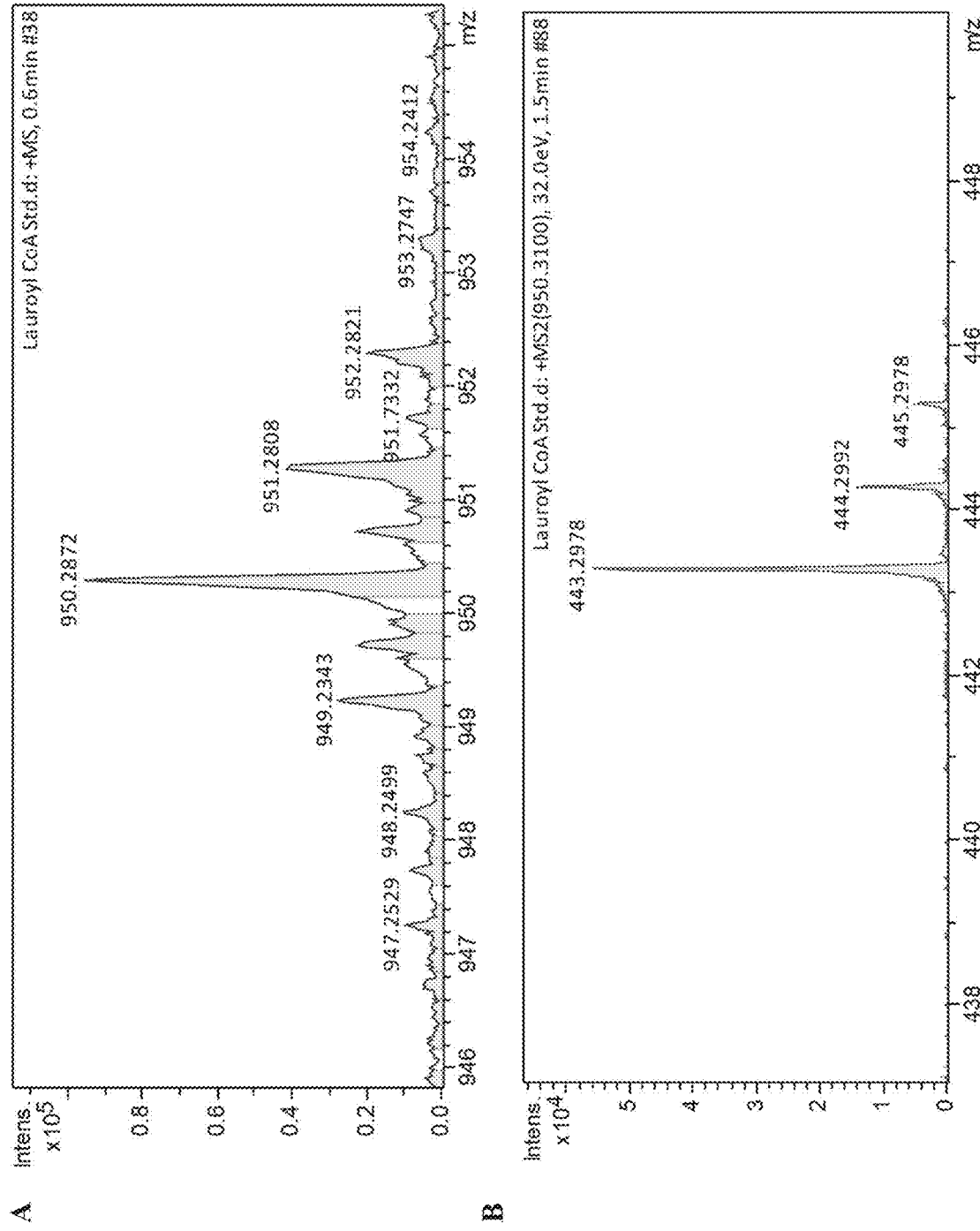
FIGS. 15A-15B demonstrate (A) MS parent ion peak (950 Da) for a 20 μM Lauroyl-CoA standard put through the entire extraction and purification process; and (B) MS/MS peak for Lauroyl-CoA (443 Da) obtained through collision of the parent ion of 950 Da after a neutral loss of 507 Da.

Lauroyl-CoA Standard. FIGS. 15A-15B show the results for a 20 μM standard put through the entire extraction and purification process in both MS (FIG. 16A) and MS/MS (FIG. 16B) mode. The parent ion of Lauroyl-CoA is 950 and the MS-MS peak is thus 443 after a neutral loss of 507 Da. These results demonstrate that Lauroyl-CoA is easily detected by the described extraction and quantification methods.

CONCLUSION

In summary, these data demonstrate successful introduction of a vector encoding bacterial Type I FAS into a photosynthetic organism and evidence that Type I FAS expression in the transformed organisms depletes the CoA pool but vitamin $B_5$ supplementation or other means by which CoA production can be enhanced, improves acyl-CoA production.

We claim:

1. A genetically modified photosynthetic *Synechocystis* sp. PCC 6803 bacterium which produces activated acyl-CoA, the *Synechocystis* sp. PCC 6803 bacterium comprising one or more transgenes expressing a heterologous bacterial fatty acid synthase type I (FAS I) from *Rhodococcus fascians* (*R. fascians*) D188 and a heterologous acyl carrier protein synthase (acpS) from *Rhodococcus fascians* (*R. fascians*) D188 driven by a nickel-inducible promoter, wherein the genetically modified photosynthetic *Synechocystis* sp. PCC 6803 bacterium is capable of increased production of activated acyl-CoA compared to a genetically unmodified photosynthetic *Synechocystis* sp. PCC 6803 bacterium, wherein the genetically unmodified photosynthetic *Synechocystis* sp. PCC 6803 bacterium does not express endogenous FAS I.

2. The genetically modified bacterium of claim 1, wherein the bacterium comprises multiple copies of the one or more transgenes.

3. A genetically modified *Synechocystis* sp. PCC 6803 strain expressing a transgene encoding a heterologous bacterial fatty acid synthase type I (FAS I) from *Rhodococcus fascians* (*R. fascians*) D188 driven by a nickel-inducible promoter heterologous to the FAS I coding sequence and capable of driving expression within the *Synechocystis* sp. PCC 6803 strain; wherein the modified *Synechocystis* sp. PCC 6803 strain is capable of increased production of activated acyl-CoA compared to an unmodified *Synechocystis* sp. PCC 6803 strain lacking the heterologous bacterial FAS I.

4. The genetically modified *Synechocystis* sp. PCC 6803 strain of claim 3, further comprising a transgene encoding a heterologous acyl carrier protein synthase (acpS) from *Rhodococcus fascians* (*R.fascians*) D188 driven by the nickel-inducible promoter.

* * * * *